(12) United States Patent
Wenzel et al.

(10) Patent No.: US 8,504,152 B2
(45) Date of Patent: *Aug. 6, 2013

(54) SYSTEM AND METHOD FOR ESTIMATING CARDIAC PRESSURE BASED ON CARDIAC ELECTRICAL CONDUCTION DELAYS USING AN IMPLANTABLE MEDICAL DEVICE

(75) Inventors: Brian Jeffrey Wenzel, San Jose, CA (US); Dan E. Gutfinger, Irvine, CA (US); Mihir Naware, San Jose, CA (US); Xiaoyi Min, Thousand Oaks, CA (US); Jeffery Siou, San Jose, CA (US); Anders Bjorling, Solna (SE); Dorin Panescu, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1133 days.

This patent is subject to a terminal disclaimer.

(21) Appl. No.: 11/779,350

(22) Filed: Jul. 18, 2007

(65) Prior Publication Data

US 2009/0018597 A1 Jan. 15, 2009

Related U.S. Application Data

(60) Provisional application No. 60/910,060, filed on Apr. 4, 2007.

(51) Int. Cl.
*A61N 1/365* (2006.01)
(52) U.S. Cl.
USPC .............. 607/23; 600/513; 600/514; 600/515
(58) Field of Classification Search
USPC .................................. 607/23; 600/513–516
See application file for complete search history.

(56) References Cited

U.S. PATENT DOCUMENTS

| 5,003,976 A | 4/1991 | Alt |
| 5,476,483 A | 12/1995 | Bornzin et al. |

(Continued)

FOREIGN PATENT DOCUMENTS

| EP | 1629863 A1 | 3/2006 |
| WO | 2005000206 A2 | 1/2005 |

(Continued)

OTHER PUBLICATIONS

McClean et al., "Noninvasive Calibration of Cardiac Pressure Transducers in Patients with Heart Failure: An Aid to Implantable Hemodynamic Monitoring and Therapeutic Guidance", Journal of Cardiac Failure, vol. 12, No. 7, 2006, pp. 568-576.

(Continued)

*Primary Examiner* — Joseph Dietrich
(74) *Attorney, Agent, or Firm* — Theresa Raymer; Steven M. Mitchell

(57) ABSTRACT

Techniques are provided for estimating left atrial pressure (LAP) or other cardiac performance parameters based on measured conduction delays. In particular, LAP is estimated based interventricular conduction delays. Predetermined conversion factors stored within the device are used to convert the various the conduction delays into LAP values or other appropriate cardiac performance parameters. The conversion factors may be, for example, slope and baseline values derived during an initial calibration procedure performed by an external system, such as an external programmer. In some examples, the slope and baseline values may be periodically re-calibrated by the implantable device itself. Techniques are also described for adaptively adjusting pacing parameters based on estimated LAP or other cardiac performance parameters. Still further, techniques are described for estimating conduction delays based on impedance or admittance values and for tracking heart failure therefrom.

27 Claims, 20 Drawing Sheets

U.S. PATENT DOCUMENTS

| | | | |
|---|---|---|---|
| 5,676,141 | A | 10/1997 | Hollub |
| 5,836,985 | A | 11/1998 | Rostami et al. |
| 6,044,297 | A | 3/2000 | Sheldon et al. |
| 6,249,705 | B1 | 6/2001 | Snell |
| 6,328,699 | B1 | 12/2001 | Eigler et al. |
| 6,424,865 | B1 | 7/2002 | Ding |
| 6,438,408 | B1 | 8/2002 | Mulligan et al. |
| 6,480,733 | B1 | 11/2002 | Turcott |
| 6,512,952 | B2 | 1/2003 | Stahmann et al. |
| 6,522,923 | B1 | 2/2003 | Turcott |
| 6,572,557 | B2 | 6/2003 | Tchou et al. |
| 6,628,988 | B2 | 9/2003 | Kramer et al. |
| 6,643,546 | B2 | 11/2003 | Mathis et al. |
| 6,643,548 | B1 | 11/2003 | Mai et al. |
| 6,645,153 | B2 | 11/2003 | Kroll et al. |
| 6,668,194 | B2 | 12/2003 | VanHout |
| 6,741,885 | B1 | 5/2004 | Mai et al. |
| 6,748,261 | B1 | 6/2004 | Kroll |
| 6,763,267 | B2 | 7/2004 | Ding |
| 6,970,742 | B2 | 11/2005 | Mann et al. |
| 7,115,095 | B2 | 10/2006 | Eigler et al. |
| 7,231,250 | B2 * | 6/2007 | Band et al. .................. 607/18 |
| 7,248,925 | B2 | 7/2007 | Bruhns et al. |
| 7,383,086 | B2 | 6/2008 | Ding |
| 2003/0144703 | A1 * | 7/2003 | Yu et al. .................. 607/17 |
| 2004/0019285 | A1 | 1/2004 | Eigler et al. |
| 2004/0147969 | A1 | 7/2004 | Mann et al. |
| 2005/0038477 | A1 * | 2/2005 | Kramer et al. .................. 607/9 |
| 2005/0125041 | A1 | 6/2005 | Min et al. |
| 2005/0131480 | A1 * | 6/2005 | Kramer et al. .................. 607/30 |
| 2005/0165456 | A1 | 7/2005 | Mann et al. |
| 2005/0177194 | A1 | 8/2005 | Bjorling |
| 2005/0215914 | A1 | 9/2005 | Bornzin et al. |
| 2006/0009810 | A1 | 1/2006 | Mann et al. |
| 2006/0079793 | A1 | 4/2006 | Mann et al. |
| 2006/0136002 | A1 * | 6/2006 | Sheth et al. .................. 607/27 |
| 2006/0149324 | A1 | 7/2006 | Mann et al. |
| 2006/0149330 | A1 | 7/2006 | Mann et al. |
| 2006/0149331 | A1 | 7/2006 | Mann et al. |

FOREIGN PATENT DOCUMENTS

| | | |
|---|---|---|
| WO | 2005000206 A3 | 1/2005 |
| WO | 2006104868 A1 | 10/2006 |

OTHER PUBLICATIONS

Helfant et al., "Effect of Sustained Isometric Handgrip Exercise on Left Ventricular Performance," Circulation 1971;44:982.

* cited by examiner

SYSTEM AND METHOD FOR ESTIMATING CARDIAC PRESSURE BASED ON CARDIAC ELECTRICAL CONDUCTION DELAYS USING AN IMPLANTABLE MEDICAL DEVICE

RELATED APPLICATIONS

This application is related to U.S. patent application Ser. No. 11/779,380 of Wenzel et al., entitled, "System and Method for Estimating Cardiac Pressure Based on Cardiac Electrical Conduction Delays Using An Implantable Medical Device," now US Publication No. 2009/0287267, filed concurrently with this application. This application also claims priority on U.S. Provisional Patent Application No. 60/910,060 of Wenzel et al., entitled, "System and Method for Estimating Left Atrial Pressure based on Intra-Cardiac Conduction Time Delays," filed Apr. 4, 2007, which is fully incorporated by reference herein.

FIELD OF THE INVENTION

The invention relates generally to implantable medical devices such as pacemakers and implantable cardioverter defibrillators (ICDs) and in particular to techniques for estimating cardiac pressure (particularly left atrial pressure (LAP)) to detect and evaluate heart failure and related conditions and to automatically adjust pacing parameters or the like.

BACKGROUND OF THE INVENTION

Heart failure is a debilitating disease in which abnormal function of the heart leads to inadequate blood flow to fulfill the needs of the tissues and organs of the body. Typically, the heart loses propulsive power because the cardiac muscle loses capacity to stretch and contract. Often, the ventricles do not adequately fill with blood between heartbeats and the valves regulating blood flow become leaky, allowing regurgitation or back-flow of blood. The impairment of arterial circulation may deprive vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds cardiac muscle mass causing the ventricles to grow in volume in an attempt to pump more blood with each heartbeat, i.e. to increase the stroke volume. This places a still higher demand on the heart's oxygen supply. If the oxygen supply falls short of the growing demand, as it often does, further injury to the heart may result, typically in the form of myocardial ischemia or myocardial infarction. The additional muscle mass may also stiffen the heart walls to hamper rather than assist in providing cardiac output. Often, electrical and mechanical dyssynchronies develop within the heart such that the various chambers of the heart no longer beat in a synchronized manner, degrading overall cardiac function. A particularly severe form of heart failure is congestive heart failure (CHF) wherein the weak pumping of the heart or compromised filling leads to build-up of fluids in the lungs and other organs and tissues.

Many patients susceptible to CHF, particularly the elderly, have pacemakers, ICDs or other implantable medical devices implanted therein, or are candidates for such devices. Accordingly, it is desirable to provide techniques for detecting and tracking CHF using such devices. One particularly effective parameter for detecting and tracking CHF is cardiac pressure, particularly LAP, i.e. the blood pressure within the left atrium of the patient. Reliable detection or estimation of LAP would not only permit the implanted device to track CHF for diagnostic purposes but to also control therapies applied to address CHF such as cardiac resynchronization therapy (CRT). CRT seeks to normalize asynchronous cardiac electrical activation and the resultant asynchronous contractions by delivering synchronized pacing stimulus to the ventricles using pacemakers or ICDs equipped with biventricular pacing capability. The pacing stimulus is typically synchronized so as to help to improve overall cardiac function. This may have the additional beneficial effect of reducing the susceptibility to life-threatening tachyarrhythmias. CRT and related therapies are discussed in, for example, U.S. Pat. No. 6,643,546 to Mathis, et al., entitled "Multi-Electrode Apparatus And Method For Treatment Of Congestive Heart Failure"; U.S. Pat. No. 6,628,988 to Kramer, et al., entitled "Apparatus And Method For Reversal Of Myocardial Remodeling With Electrical Stimulation"; and U.S. Pat. No. 6,512,952 to Stahmann, et al., entitled "Method And Apparatus For Maintaining Synchronized Pacing".

Reliable estimates of LAP provided by a pacemaker or ICD would also allow the dosing of heart failure medications (such as diuretics) to be properly titrated so as to minimize the number of episodes of acute heart failure decompensation. Another advantage to providing reliable estimates of LAP is that physicians are typically familiar with LAP values. Hence, LAP estimates could be provided to the physician via diagnostic displays, which the physicians can then readily interpret.

However, LAP is a difficult parameter to detect since it is not clinically appealing to place a blood pressure sensor directly in the left atrium due to the chronic risk of thromboembolic events, as well as risks associated with the trans-septal implant procedure itself. Accordingly, various techniques have been developed for estimating LAP based on other parameters that can be more safely sensed by a pacemaker or ICD. In this regard, a number of techniques have been developed that use electrical impedance signals to estimate LAP. For example, impedance signals can be sensed along a sensing vector passing through the left atrium, such as between an electrode mounted on a left ventricular (LV) lead and another electrode mounted on a right atrial (RA) lead. The sensed impedance is affected by the blood volume inside the left atrium, which is in turn reflected by the pressure in the left atrium. Accordingly, there is a correlation between the sensed impedance and LAP, which can be exploited to estimate LAP and thereby also track CHF. See, for example, U.S. Provisional Patent Application No. 60/787,884 of Wong et al., entitled, "Tissue Characterization Using Intracardiac Impedances with an Implantable Lead System," filed Mar. 31, 2006, and U.S. patent application Ser. Nos. 11/558,101, 11/557,851, 11/557,870, 11/557,882 and 11/558,088, each entitled "Systems and Methods to Monitor and Treat Heart Failure Conditions", of Panescu et al. See, also, U.S. patent application Ser. No. 11/558,194, by Panescu et al., entitled "Closed-Loop Adaptive Adjustment of Pacing Therapy based on Cardiogenic Impedance Signals Detected by an Implantable Medical Device." Particularly effective techniques for calibrating impedance-based techniques are set forth in: U.S. patent application Ser. No. 11/559,235, by Panescu et al., entitled "System and Method for Estimating Cardiac Pressure Using Parameters Derived from Impedance Signals Detected by an Implantable Medical Device."

It would be desirable to develop LAP estimation techniques that do not rely only on impedance but instead, or additionally, exploit intracardiac electrogram (IEGM) signals commonly sensed by pacemakers and ICDs, and it is to that end that certain aspects of the present invention are directed. Also, it would be desirable to provide techniques for automatically adjusting and controlling CRT and other forms of cardiac rhythm management therapy in response to estimated LAP so as to, e.g., mitigate the effects of CHF, and it is to that end that other aspects of the present invention are directed.

SUMMARY OF THE INVENTION

In accordance with an exemplary embodiment, a method and system are provided for estimating cardiac pressure within a patient using an implantable medical device. Briefly, an electrical conduction delay is measured in the heart of the patient that is affected by cardiac pressure. Then, cardiac pressure is estimated within the patient based on the conduction delay. In this regard, when a particular chamber of the heart is stimulated, cardiac contraction occurs in the stimulated chamber, and this is usually followed by a subsequent cardiac contraction in other chamber(s) later in time after the stimulus has had sufficient time to reach the other chamber(s). The conduction time delay between contractions of any two chambers is dependent on various factors, such as conduction velocity and the distance needed to be traveled. The conduction time delay between the contraction of any two cardiac chambers following either a natural occurring stimulus or an externally administered stimulus is indicative, in at least some patients, of the degree of cardiac failure, such that longer delays may be associated with a worsening cardiac status. Moreover, the conduction time delay is, in at least some patients, proportional to the cardiac chamber size and further indicative of the intracardiac chamber pressure, such that the conduction time delay may be advantageously exploited to estimate or predict the intra-cardiac chamber pressure, at least within such patients.

In one example, conduction delays from the left ventricle (LV) to the right ventricle (RV) are measured by applying a cardiac pacing pulse (i.e. a V-pulse) to the LV using one or more LV electrodes and then sensing the subsequent electrical depolarization in the RV using one or more RV electrodes. The intrinsic electrical depolarization in the RV may be detected based on the timing of a QRS-complex sensed within an RV IEGM. The delay between the V-pulse delivered to the LV and the peak of the RV QRS-complex is then taken as an estimate of the LV-RV interventricular conduction delay. In another example, conduction delays from the LV to the RV are measured by sensing an intrinsic QRS-complex in both an LV IEGM and an RV IEGM. The delay between the LV QRS-complex and the RV QRS-complex is taken as the estimate of the LV-RV interventricular conduction delay. In other examples, the RV is paced first and the delay from the RV to the LV is measured. In still other examples, rather than using LV-RV delays, other AV delays are employed. For example, AV delays may be obtained based on paced or sensed events or based on P-wave morphology (e.g. based on the shape or width of the P-wave) or based on the morphology of atrial evoked responses.

Predetermined conversion factors are then input from memory for converting the measured conduction delay to LAP values or other cardiac pressure values. The conversion factors may be, for example, slope and baseline values derived using, e.g., linear regression techniques. Then, LAP or other cardiac pressure values are estimated within the patient by applying the conversion factors to the conduction delay. For example, cardiac pressure may estimated using:

$$\text{Cardiac Pressure} = \text{Delay} * \text{Slope} + \text{Baseline}$$

where Delay is the measured conduction delay and Slope and Baseline are the conversion factors appropriate to the pressure value being estimated and the chambers through which the conduction delay is measured. For the case where LAP is estimated from the LV-RV conduction delay:

$$qLAP_{LV-RV} = D_{LV-RV} * \text{Slope}_{LAP/LV-RV} + \text{Baseline}_{LAP/LV-RV}$$

where $D_{LV-RV}$ is the measured conduction delay between the LV and the RV, $\text{Slope}_{LAP/LV-RV}$ and $\text{Baseline}_{LAP/LV-RV}$ are the conversion factors appropriate to LAP when estimated based on the LV-RV conduction delay, and $qLAP_{LV-RV}$ is the resulting estimate of LAP. Note that the baseline value will be in units of LAP. The LV-RV subscript is applied so as to distinguish baseline values for use in estimating LAP from LV-RV delays from other baseline values for use in estimating LAP based on other delays. However, it should be understood that the use of such subscripts is an arbitrary terminology choice and hence has no effect on the scope of the claimed subject matter. The "q" of qLAP is employed to distinguish the resulting estimate from the estimates made using the impedance-based techniques discussed above in the *Panescu* et al. patent applications (i.e. ZLAP estimates or eLAP.) Again, it should be understood that the use of the term "qLAP" is an arbitrary terminology choice and hence has no effect on the scope of the claimed subject matter. In many of the illustrative examples described herein, a QuickOpt technique is employed to determine the conduction delays. QuickOpt is a trademark of St. Jude Medical. QuickOpttechniques are described more fully in U.S. Patent Application No. 2005/0125041 of Min et al., published Jun. 9, 2005, entitled "Methods for Ventricular Pacing." The subscript "LV-RV" is applied to qLAP to indicate that the estimate is derived from an LV-RV conduction delay. LAP may potentially be estimated from other conduction delay values as well, such as AV delays.

The pressure value estimated in the foregoing example (and in the other examples described herein) is an effective intracardiac pressure ($P_{eff}$), not an absolute pressure. It represents the absolute intracardiac pressure less intrathoracic pressure:

$$P_{eff} = P_{intracardiac} - P_{intrathoracic}$$

That is, the effective pressure is a type of gauge pressure. Unless otherwise noted, all estimated cardiac pressure values discussed herein, particularly estimated LAP, are effective pressure values. In some techniques described herein, such as techniques where the Valsalva maneuver is exploited to reduce intracardiac pressure within the patient for the calibration purposes, the distinction between effective pressure and absolute pressure is particularly important and effective pressure should be used. In those examples, the term effective qLAP will be used as a reminder that effective pressures are used. In any case, effective pressure values are typically more useful from a clinical perspective than absolute pressure values.

In an illustrative example, the slope and baseline values ($\text{Slope}_{LAP/LV-RV}$ and $\text{Baseline}_{LAP/LV-RV}$) are determined during an initial calibration procedure based on the assumption that there is a linear relationship between $D_{LV-RV}$ and LAP. To calibrate the slope and baseline values for a particular patient, a first delay calibration value ($D_{LV-RV/1}$) and a corresponding first cardiac pressure calibration value ($LAP_1$) are measured within the patient at a first point in time. Then, a second delay calibration value ($D_{LV-RV/2}$) and a corresponding second cardiac pressure calibration value ($LAP_2$) are measured at a second point in time within the patient. The first and second pressure calibration values ($LAP_1$, $LAP_2$) may be measured within the patient using, e.g., a Swan-Ganz catheter equipped to measure pulmonary capillary wedge pressure (PCWP). The times are chosen such that the first and second cardiac pressure values ($LAP_1$, $LAP_2$) differ substantially from one another (and so the conduction delay values also differ substantially from one another). In one particular example, the first pair of calibration values ($D_{LV-RV/1}$, $LAP_1$) are detected while the patient is at rest; whereas the second calibration values ($D_{LV-RV/2}$, $LAP_2$) are detected while the patient is subject to a condition significantly affecting cardiac pressure, such as isometric muscle contraction, vasodilatation, vasoconstriction, rapid pacing or performance of the Valsalva maneuver or the handgrip maneuver by the patient. The slope value is then calibrated by calculating:

$$\text{Slope}_{LAP/LV-RV} = (LAP_2 - LAP_1)/(D_{LV-RV/2} - D_{LV-RV/1}).$$

The baseline value is calibrated by calculating:

$$\text{Baseline}_{LAP/LV-RV} = LAP_2 - \text{Slope}_{LAP/LV-RV} * D_{LV-RV/1}.$$

Alternatively, a plurality of calibration values can instead be obtained within the patient, with the slope and baseline values then calculated for that particular patient using linear regression techniques. In still other implementations, calibration values are instead obtained within test subjects, with the calibration values then employed to estimate LAP within other patients. For example, a plurality of calibration values can be obtained within a population of test subjects (particularly ones in which heart failure is progressing), with the slope and baseline values then calculated using linear regression techniques from the data obtained from the test subjects. By using test subjects in which heart failure is progressing, LAP likewise increases within the test subjects, yielding a range of pressure values suitable for linear regression analysis. The slope and baseline values obtained from the test subjects can be used, at least, as starting values for use in estimating LAP within other patients, with those parameters then potentially optimized for use in the particular patient. Still further, linear models relating cardiac pressure and conduction delays need not necessarily be used, i.e. more sophisticated correlation models may instead by used such as neural networks. Linear models are preferred in view of their simplicity.

The baseline value, once determined, may change over time within a particular patient. Accordingly, it may be desirable within some patients to occasionally re-calibrate the baseline value. To re-calibrate the baseline value, an additional conduction delay calibration value ($D_{LV-RV/N}$) is measured while the patient performs a Valsalva maneuver. During the Valsalva maneuver, the chambers of the heart are substantially emptied of blood such that the effective cardiac blood pressure, particularly effective LAP or effective right atrial pressure (RAP), is reduced to near zero secondary to reduced venous return, especially in patients that have at rest moderate to low cardiac filling pressures (<20 mmHg) with the absence of significant diastolic dysfunction or non-compliance of the heart. Under the assumption that the effective LAP drops to zero in the late Phase II of the Valsalva maneuver (i.e., during the interval from 5 seconds to 10 seconds following the initiation of the strain), the baseline value to be updated by the implanted device using only the newly detected conduction delay value, i.e. ($\text{Baseline}_{LAP/LV-RV}$) may be updated using:

$$\text{Baseline}_{LAP/LV-RV} = -\text{Slope}_{LAP/LV-RV} * D_{LV-RV/N}.$$

In other implementations, both the slope and baseline values are re-calibrated by the implanted device based on newly detected conduction delay values. In still other implementations, to account for the fact that the effective LAP does not reach zero completely during the Valsalva maneuver in some patients (such as heart failure patients with high cardiac filling pressures >20 mmHg and/or with poor cardiac compliance), an additional correction term may be obtained during initial calibration that is used to correct or adjust the re-calibrated values. Preferably, re-calibration is performed while the patient is clinically stable. Moreover, in at least some patients, Valsalva-based re-calibration techniques may not achieve precise calibration due to these factors. Within those patients, other re-calibration techniques are preferably used, which do not necessarily exploit the Valsalva maneuver. In general, any maneuver or condition that significantly affects cardiac pressure within the patient might be exploited for re-calibration purposes. Examples include one or more of: isometric muscle contraction, vasodilatation, vasoconstriction, rapid pacing and performance of the handgrip maneuver. The handgrip maneuver tends to acutely increase LAP. See, e.g., Helfant et al., "Effect of Sustained Isometric Handgrip Exercise on Left Ventricular Performance," Circulation. 1971;44:982. LAP may be estimated using the Swan-Ganz catheter. In some cases, it may be appropriate to employ multiple re-recalibration techniques each yielding new Slope and Baseline values, which are then averaged together to yield the re-calibrated values.

Also, in the illustrative example, therapy is controlled based on the estimated LAP (e.g. based on qLAP), particularly so as to reduce LAP. The therapy to be adjusted may be pacing therapy. For example, pacing timing parameters such as the atrioventricular (AV) pacing delay and the interventricular (LV-RV) pacing delay may be adjusted. Within systems equipped to provide pacing at different locations within the same chamber, intraventricular ($LV_1$-$LV_2$), intra-atrial ($LA_1$-$LA_2$) delay values may additionally or alternatively be adjusted. Alternatively, multi-site pacing systems could switch to different pacing configurations or use different pacing electrodes in order to keep the LAP estimate, qLAP, within a safe or hemodynamically stable range. Preferably, the adjustments are adaptive, i.e. the adjustments are performed in a closed-loop so as to adapt the adjustments to changes in estimated LAP so as to optimize therapy. By adjusting pacing parameters based on estimated LAP, the parameters can be promptly adjusted to immediately respond to changes within the heart that affect LAP, such as any deterioration in mechanical synchrony arising due to CHF, conduction defects or other ailments such as myocardial infarction or acute cardiac ischemia. Moreover, by adaptively adjusting the pacing parameters based on estimated LAP, the direction and/or magnitude of the adjustments need not be pre-determined. That is, it need not be known in advance whether a particular pacing parameter should be increased or decreased in response to deterioration in LAP. Adaptive adjustment allows the direction and magnitude of any adjustments to the pacing parameters to be automatically optimized. Thus, if an initial increase in a particular pacing parameter causes a further deterioration in LAP, the pacing parameter may then be automatically decreased in an attempt to improve LAP. If neither an increase nor a decrease in a particular pacing parameter significantly affects LAP, then a different pacing parameter may be selected for adaptive adjustment.

The adaptive adjustment of pacing therapy using estimated LAP may be performed in conjunction with one or more impedance-based adjustments techniques, such as those set forth in the above-cited applications of Panescu et al. For example, a mechanical dyssynchrony may derived from the cardiogenic impedance signals while an estimate of LAP is derived from conduction delays, permitting both to be used in adjusting the pacing parameters. Also, impedance signals may be used to derive electrical conduction delays from which LAP may be also estimated. Still further, if the implanted device may be equipped with a sensor to directly measure another cardiac pressure value besides LAP (e.g., LV end diastolic ($LV_{END}$) pressure), then such pressure measurements may be used in conjunction with the LAP estimates to adjust pacing parameters so as to reduce both measures of pressure. In some implementations, the pacing parameters are adaptively adjusted only when the patient is in certain predetermined states as determined by activity sensor, posture detectors, etc. In one particular example, adaptive adjustment is only performed if the patient is at rest and in a supine posture. Adaptive adjustment may be still further limited to times when the blood oxygen saturation ($SO_2$) level of the patient is within a certain acceptable range. Yet as a different embodiment, admittance or impedance measurements could be used to estimate AV or VV delays. As the heart tends to enlarge with heart failure progression, conduction delays tend to increase whereas impedance values tend to decrease. Therefore, admittance or values could be used to estimate AV or VV delays. A calibration step may be required depending upon the implementation. If required, calibration consists of determining delays using known techniques (such as based on electrograms, as presented above) and applying the calibration results to the microprocessor-based procedure that estimates delays from impedance. Pacing therapy can then be adjusted to control the estimated delays within a safe or stable range about a baseline.

Thus, various techniques are provided for estimating or predicting LAP for use, e.g., in automatically adjusting pacing therapy and for detecting and tracking heart failure. Individual implantable systems may be equipped to perform some or all of these techniques. In some examples, LAP is determined by combining estimates derived from the various individual techniques. Heart failure is then detected based on the combined LAP estimate. Upon detecting of the onset of heart failure, appropriate warning signals may be generated for alerting the patient to consult a physician. The warning signals can include "tickle" warning signals applied to subcutaneous tissue and short range telemetry warning signals transmitted to a warning device external to the patient such as a bedside monitor. The warning signals, as well as appropriate diagnostic information (such as the estimated LAP values), are preferably forwarded to the physician by the bedside monitor. Various other forms of therapy may also be automatically applied or modified by the implanted system in response to heart failure, depending upon the capabilities of the system. For example, if the device is equipped to perform CRT, then CRT pacing may be initiated or otherwise controlled based on LAP. Also, if the implanted system is equipped with a drug pump, appropriate medications (such as diuretics) potentially may be administered directly to the patient, depending upon the programming of the system. Alternatively, the estimated LAP may be presented directly to the patient using a handheld or a bedside monitor, so that the patients may utilize the estimated LAP reading to self-titrate oral dosages of heart failure medications based on a sliding scale prescription that was provided to the patient in advance. This concept is similar to the self-titration of insulin dosage based on a measured blood sugar from a glucometer using a prescribed insulin sliding scale.

Although summarized with respect to estimating LAP based on LV-RV conduction delays, the techniques of the invention may be applied to estimating other parameters from the same or different conduction delays. For example, LV end diastolic volume (EDV) or LV end diastolic pressure (EDP) may also be estimated, at least within some patients, based on LV-RV conduction delays by using appropriate calibration factors (e.g. $Slope_{LV\ EDV/LV-RV}$, $Baseline_{LV\ EVD/LV-RV}$ or $Slope_{LV\ EDP/LV-RV}$, $Baseline_{LV\ EVP/LV-RV}$). As another example, LAP may instead be estimated, within at least some patients, based on AV conduction delays by using appropriate calibration factors (e.g. $Slope_{LAP/AV}$, P-wave morphology or width, $Baseline_{LAP/AV}$). As yet another example, LAP may instead be estimated, within at least some patients, based on intraventricular conduction delays by using appropriate calibration factors (e.g. $Slope_{LAP/LV1-LV2}$, $Baseline_{LAP/LV1-LV2}$), particularly if the locations of the LV1 and LV2 sensing/pacing locations are fairly widely separated within the LV. Thus, a variety of cardiac chamber parameters may be estimated based on a variety of cardiac electrical conduction delays. LAP is generally preferred as it is strongly correlated with CHF. LV-RV conduction delays may be preferred, as such delays provide perhaps the most effective delay for use in estimating LAP. However, in at least some patients, other conduction delays might instead be preferred for use in estimating other cardiac performance parameters.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Medical System

Figure 1:
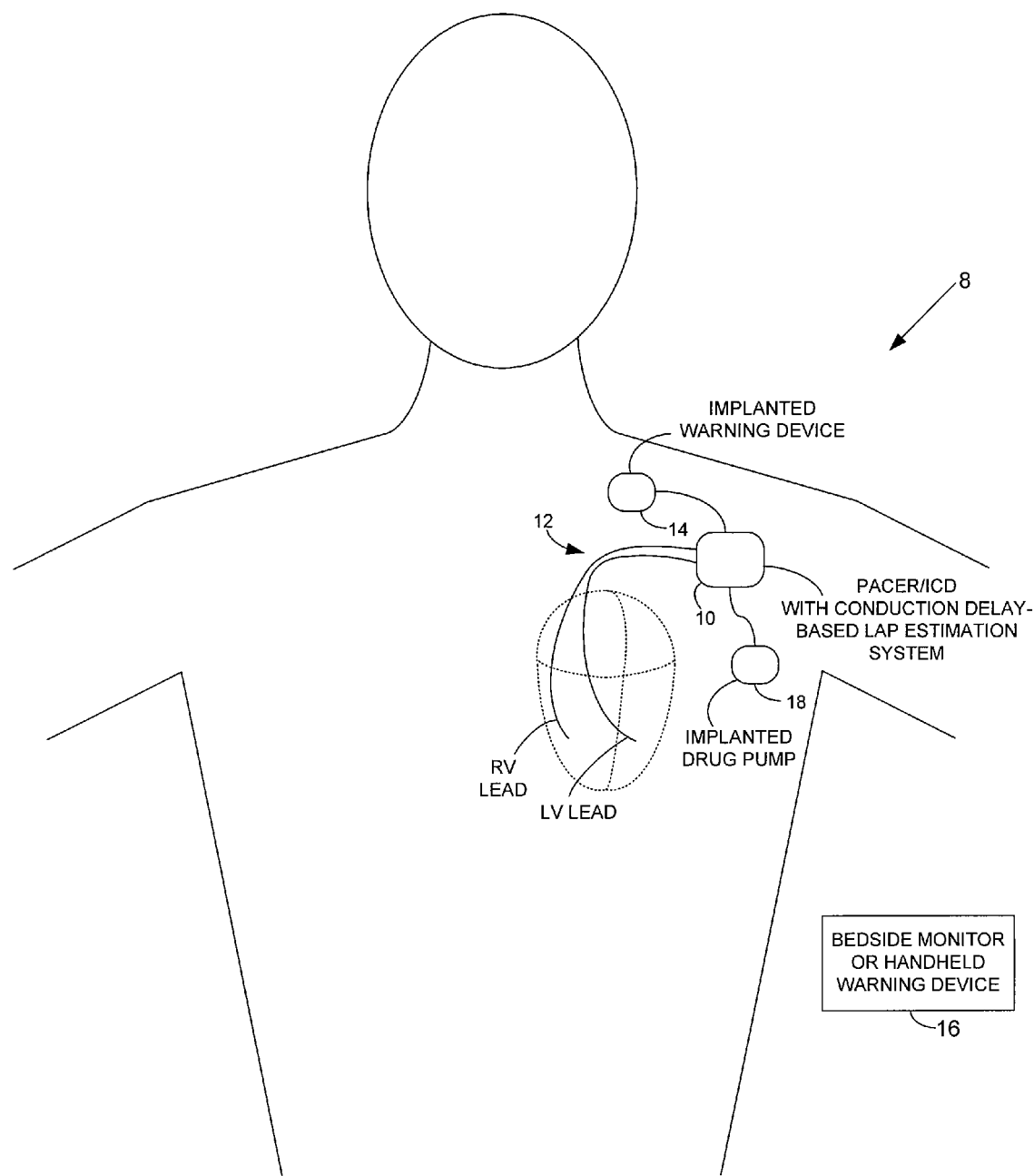
FIG. 1 is a stylized representation of an exemplary implantable medical system equipped with a conduction delay-based LAP estimation system.
Figure 14:
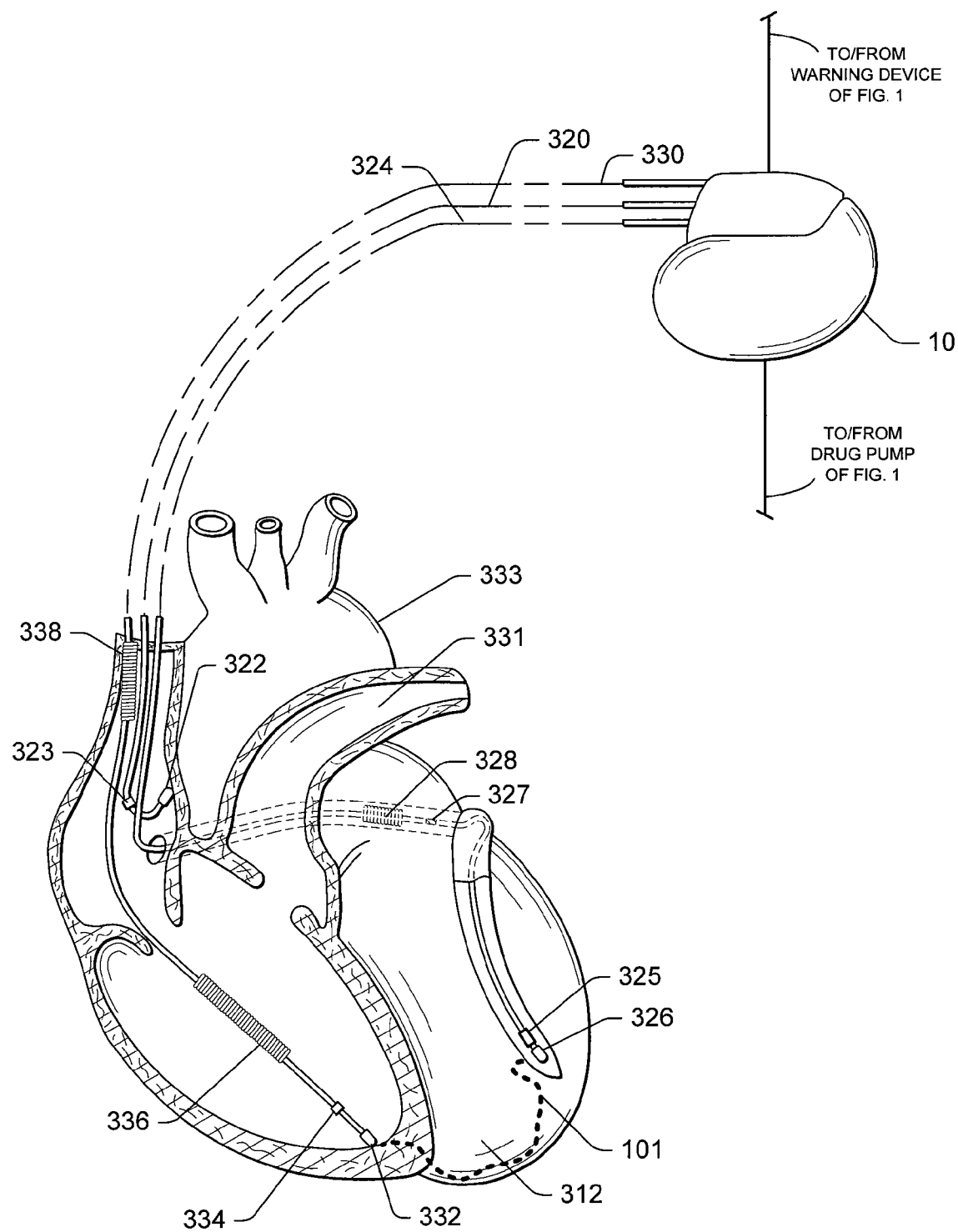
FIG. 14 is a simplified, partly cutaway view, illustrating the pacer/ICD of FIG. 1 along with a more complete set of leads implanted in the heart of the patient.

FIG. 1 provides a stylized representation of an exemplary implantable pacing medical system 8 capable of detecting electrical conduction delays within the heart of the patient and estimating LAP based on the conduction delays. To this end, implantable system 8 includes a pacer/ICD 10 or other cardiac stimulation device that incorporates internal components (shown individually in FIG. 15, and discussed below) for detecting one or more conduction delays using electrodes mounted to a set of sensing/pacing leads 12 and for estimating LAP or other cardiac performance parameters based on the conduction delays. In FIG. 1, only two leads are shown. A more complete set of leads is illustrated in FIG. 14, which is discussed below. Within many of the exemplary implementations described herein, LAP is estimated based on LV-RV delays detected by the pacer/ICD. However, other conduction delays can be exploited, alone or in combination, to estimate other cardiac pressure values or other cardiac performance parameters, such as EDV. LAP is emphasized as it is correlated with CHF. Predetermined conversion factors stored within the pacer/ICD are used to convert the conduction delays into LAP values or other appropriate cardiac chamber parameters. The conversion factors may be, for example, slope and baseline values derived during an initial calibration procedure performed by an external system, such as an external programmer (FIG. 16.) As will be explained, the baseline value may be periodically re-calibrated by the pacer/ICD itself. The slope value is assumed to remain substantially unchanged such that re-calibration of the slope is typically not required.

Figure 2:
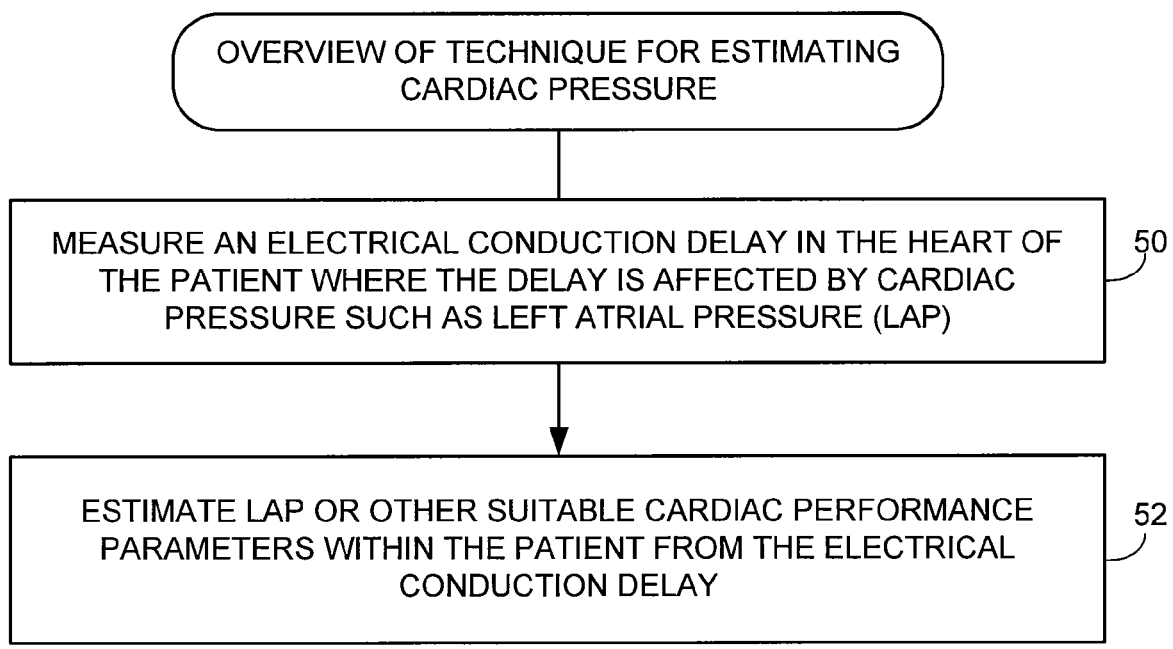
FIG. 2 is a flow diagram providing a broad overview of conduction delay-based cardiac pressure estimation techniques that may be performed by the system of FIG. 1.

FIG. 2 provides a broad summary of the cardiac pressure estimation techniques that may be performed by the pacer/ICD of FIG. 1. At step 50, the pacer/ICD measures an electrical conduction delay in the heart of the patient where the delay is affected by cardiac pressure such as left atrial pressure (LAP). At step 52, the pacer/ICD then estimates LAP or other suitable cardiac chamber values within the patient from the electrical conduction delay. The pacer/ICD of FIG. 1 is also equipped to track changes in the estimated LAP values so as to detect and track CHF and to adjust pacing parameters in an effort to mitigate CHF, such as CRT parameters. Techniques for performing CRT are discussed in the patents to Mathis, et al., Kramer, et al., to Stahmann, et al., cited above. Adaptively adjustment techniques set forth in the Panescu et al. patent application, "Closed-Loop Adaptive Adjustment of Pacing Therapy based on Cardiogenic Impedance Signals Detected by an Implantable Medical Device," cited above, may be exploited. Additionally or alternatively, the pacer/ICD may issue warning signals, if warranted. For example, if the estimated LAP exceeds a threshold indicative of CHF, warning signals may be generated to warn the patient, using either an implanted warning device 14 or an external bedside monitor/handheld warning device 16. Internal warning device 14 may be a vibrating device or a "tickle" voltage device that, in either case, provides perceptible stimulation to the patient to alert the patient so that the patient may consult a physician. In one example, once the tickle warning is felt, the patient positions an external warning device above his or her chest. The handheld device receives short-range telemetry signals from the implanted device and provides audible or visual verification of the warning signal. The handheld warning device thereby provides confirmation of the warning to the patient along with a display of the estimated LAP, who may be otherwise uncertain as to the reason for the internally generated warning signal. For further information regarding this warning/notification technique, see U.S. patent application Ser. No. 11/043,612, of Kil et al., filed Jan. 25, 2005, entitled "System and Method for Distinguishing among Ischemia, Hypoglycemia and Hyperglycemia using an Implantable Medical Device."

If a bedside monitor is provided, the bedside monitor provides audible or visual alarm signals to alert the patient or caregiver, as well as textual or graphic displays. In addition, diagnostic information pertaining to the deteriorating cardiac condition is transferred to the bedside monitor or is stored within the pacer/ICD for subsequent transmission to an external programmer (not shown in FIG. 1) for review by a physician or other medical professional. The physician may then prescribe any other appropriate therapies to address the condition. The physician may also adjust the operation of the pacer/ICD to activate, deactivate or otherwise control any therapies that are automatically applied. The bedside monitor may be directly networked with a centralized computing system, such as the HouseCall™ system of St. Jude Medical, for immediately notifying the physician of any significant increase in LAP. Networking techniques for use with implantable medical systems are set forth, for example, in U.S. Pat. No. 6,249,705 to Snell, entitled "Distributed Network System for Use with Implantable Medical Devices".

In addition to CRT, other forms of therapy may also be controlled by the pacer/ICD in response to changes in LAP. In this regard, if the implanted system is equipped with a drug pump, appropriate medications may be automatically administered upon detection of a significant increase in LAP due to heart failure. For example, heart failure medications may be delivered directly to the patient via the drug pump, when needed. Alternatively, if a drug pump is not available, the patient may be provided with instructions depending on the estimated LAP as to what dosage to take for various heart failure medications. Exemplary heart failure medications include angiotensin-converting enzyme (ACE) inhibitors, diuretics, nitrates, digitalis and compounds such as captopril, enalapril, lisinopril and quinapril. For example, upon detection of a high LAP level, the dosage of diuretics could be increased, either automatically via a drug pump or by sending appropriate instructions to the bedside monitor for alerting the patient or caregiver. Depending upon the particular medication, alternative compounds may be required for use in connection with an implantable drug pump. Routine experimentation may be employed to identify medications for treatment of heart failure or other conditions that are safe and effective for use in connection with an implantable drug pump. Dosages may be titrated based upon the severity of heart failure as determined from LAP.

Various techniques may be employed to confirm the detection of heart failure (or other medical conditions) made by the pacer/ICD based on the analysis of the conduction delay before drug therapy is delivered. Exemplary impedance-based heart failure detection/evaluation techniques are set forth in U.S. patent application Ser. No. 11/559,235, cited above. See, also, U.S. Pat. No. 6,748,261, entitled "Implantable medical device for and Method of Monitoring Progression or Regression of Heart Disease by Monitoring Interchamber Conduction Delays"; U.S. Pat. No. 6,741,885, entitled "Implantable Cardiac Device for Managing the Progression of Heart Disease and Method"; U.S. Pat. No. 6,643,548, entitled "Implantable medical device for Monitoring Heart Sounds to Detect Progression and Regression of Heart Disease and Method Thereof"; U.S. Pat. No. 6,572,557, entitled "System and Method for Monitoring Progression of Cardiac Disease State using Physiologic Sensors"; and U.S. Pat. No. 6,480,733, entitled "Method for Monitoring Heart Failure", each assigned to Pacesetter, Inc.

Hence, FIGS. 1 and 2 provide an overview of an implantable medical system capable of estimating LAP based on conduction delays, adjusting pacing parameters, delivering any appropriate warning/notification signals, and selectively delivering medications, when warranted. Embodiments may be implemented that do not necessarily perform all of these functions. For example, embodiments may be implemented that estimate LAP but do not automatically initiate or adjust therapy. Moreover, systems provided in accordance with the invention need not include all of the components shown in FIG. 1. In many cases, for example, the system will include only a pacer/ICD and its leads. Implantable warning devices and drug pumps are not necessarily implanted. Some implementations may employ an external monitor for displaying warning signals without any internal warning device. These are just a few exemplary embodiments. No attempt is made herein to describe all possible combinations of components that may be provided in accordance with the general principles of the invention. In addition, note that the particular locations and sizes of the implanted components shown in FIG. 1 are merely illustrative and may not necessarily correspond to actual implant locations. Although internal signal transmission lines provided are illustrated in FIG. 1 for interconnecting the various implanted components, wireless signal transmission may alternatively be employed.

Overview of Conduction Delay-Based Estimation Techniques

Figure 3:
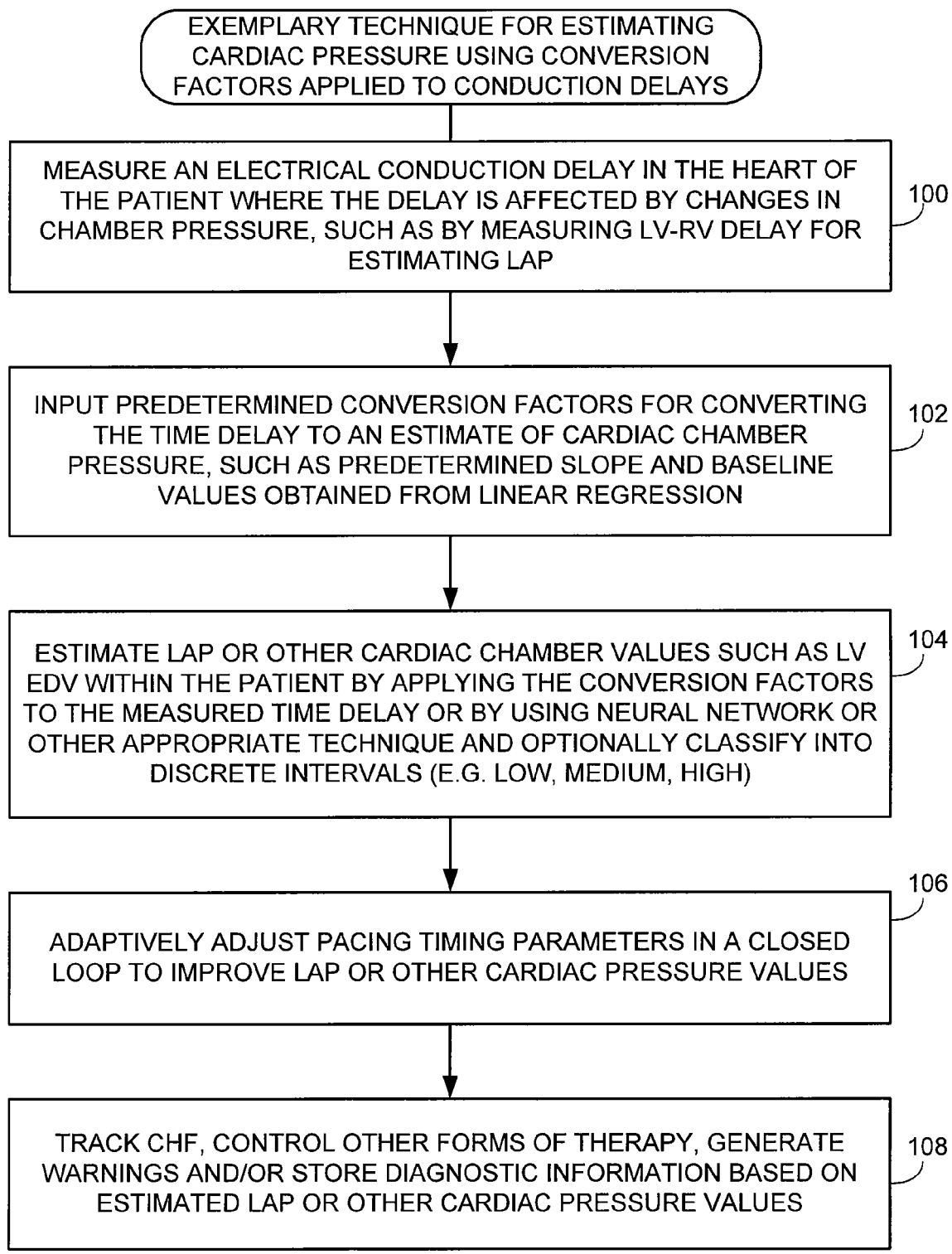
FIG. 3 is a flow diagram summarizing an illustrative technique performed in accordance with the general technique of FIG. 2 wherein cardiac pressure is estimated from conduction delays using pre-determined conversion factors and wherein pacing timing parameters are then adaptively adjusted based on the estimated pressure values.

FIG. 3 provides an overview of LAP estimation techniques that may be performed by the pacer/ICD of FIG. 1 or other implantable medical device. At step 100, the pacer/ICD measures an electrical conduction delay in the heart of the patient where the delay is affected by changes in chamber pressure, such as by measuring an interventricular LV-RV delay for use in estimating LAP. An exemplary interventricular conduction path 101 along which the delay may be measured is shown in FIG. 14, which is described more fully below. The conduction path extends through myocardial tissue between, in this particular example, a pair of LV tip and ring electrodes 426 and 425 of a coronary sinus (CS) lead 424 and a paired of RV tip and ring electrodes 424 and 434 of an RV lead 430. The tip and ring electrodes 422, 423 of a RA lead 420 are also shown. The exemplary interventricular conduction path 101 extends, as shown, down from the LV electrodes toward the apex of the ventricles and then into the RV. Once the myocardium of the LV begins to depolarize in the vicinity of the LV electrodes, electrical depolarization signals propagate along the path ultimately triggering myocardial depolarization within the RV, which is sensed using the RV electrodes. The time during which the depolarization signal propagates along this (or other) interventricular paths is the conduction time delay measured at step 100 of FIG. 3. It should be understood that the LV-RV delay may be negative, i.e. the RV may depolarize first, followed by the LV (with the RV depolarizing either naturally or due to a V-pulse delivered to the RV.) That is, depolarization signals may propagate along an interventricular conduction path from the RV to LV, instead of vice versa. Herein, for clarity, when the LV-RV delay is negative, the delay is instead typically referred to as an RV-LV delay.

The inter-ventricular conduction time delay following the delivery of a left ventricular pacing stimulus may be used to estimate LV size and/or LV filling pressure. At the time a pacing stimulus is delivered to the LV the chamber is filled with blood and corresponds to the LV EDV. The pacing stimulus will cause the LV muscle to depolarize and subsequently contract. While the LV depolarization occurs the depolarization wavefront travels across the LV toward the right ventricle and ultimately causes the RV to depolarize and subsequently contract. The delay between the time when the LV pacing stimulus was administered and the time when the RV depolarizes may be proportional to the LV EDV, which is also proportional to the LV EDP. LV EDP is a good estimate for LAP in the absence of significant mitral valve stenosis. Thus, the interventricular time delay in cardiac depolarization and/ or contraction following a ventricular stimulus may be used, at least within some patients, to estimate the end-diastolic ventricular filling volume and/or filling pressure.

Moreover, the duration of the interventricular conduction delay depends largely upon the distance over which the depolarization signal traverses, which depends, in part, on the sizes of the chambers of the heart it passes through. As heart failure progresses, pressure within the LV increases and the LV chamber often becomes distended, resulting in a generally longer conduction time delay. Hence, there is, in at least some patients, a correlation between interventricular conduction time delays and LV chamber size and LV chamber pressure. Hence, in such patients, there is a correlation between LV-RV delay and LV EDV and LV EDP. Likewise, as heart failure progresses, LAP increases. Accordingly, within at least some patients, there is also a correlation between LV-RV delay and LAP. The techniques of the invention exploit this correlation to estimate LAP from the LV-RV delay. LV EDV and LV EDP may also be estimated from the LV-RV delay.

Figure 4:
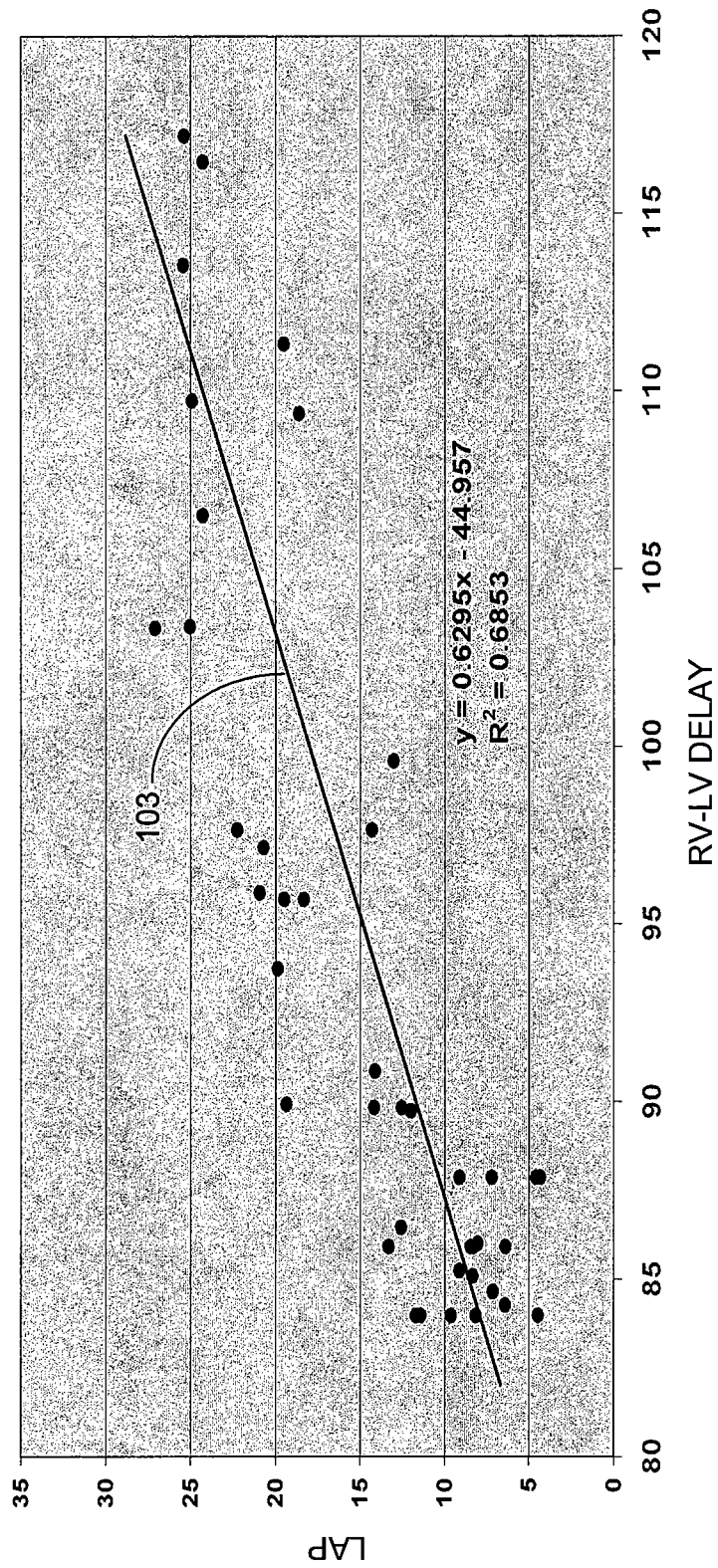
FIG. 4 is a graph illustrating a linear correlation between LAP and LV-RV delay that may be exploited by the estimation procedure of FIG. 3.

FIG. 4 illustrates data collected from a canine test subject showing the correlation between RV-LV delay (in msecs) and LAP (in mmHg). In this example, the RV-LV delay was measured based on paced RV pulses using the QuickOpt techniques, discussed below. LAP was measured using a HeartPOD LAP detection device developed by Savacor Inc., now owned by St. Jude Medical. HeartPOD is a trademark of St. Jude Medical. The canine test subject was paced via a rapid pacing protocol so as to induce and emulate heart failure, which resulted in increasing LAP values over time. As can be seen, there is a linear correlation between LAP and RV-LV delay within this test subject, as represented by linear regression line 103. Similar correlations are present in at least some, and likely most, human heart failure patients. Based on the correlation, LAP can be estimated based on RV-LV conduction delays (or LV-RV delays), at least within patients where the correlation is present.

An LV-RV conduction delay may be measured, for example, by tracking the time between when a V-pulse is delivered to the LV using the LV tip and ring electrodes and the peak of a QRS-complex sensed within the RV using the RV tip and ring electrodes. An RV-LV conduction delay may be measured, for example, by tracking the time between when a V-pulse is delivered to the RV using the RV tip and ring electrodes and the peak of a QRS-complex sensed within the LV using the LV tip and ring electrodes. However, other points within the QRS-complexes might instead be employed, such as the starting point of a complex. The peak is typically the easiest to detect. Also, instead of using the time at which a V-pulse is delivered, the pacer/ICD might instead detect and use the peak of the resulting evoked response (RV). Hence, conduction delays derived from paced events may be quantified in a variety of ways. As will be explained, conversion factors are used to convert the measured time delay into LAP or other cardiac performance values. So long as the system uses the appropriate conversion factors, the conduction delays may be measured using any suitable technique. Also, the pacer/ICD is not limited to measuring conduction delays from paced events. As another example, the conduction delay might instead be measured between the peak of a QRS-complex sensed in the LV using the tip and ring electrodes of the CS lead and the peak of the QRS-complex sensed within the RV, again using tip and ring electrodes of a RV lead. Again, the conduction delay may be quantified in a variety of ways, so long as the appropriate conversion factors are employed.

At step 102, the pacer/ICD inputs predetermined conversion factors for converting the measured time delay to an estimate of cardiac chamber pressure, such as predetermined slope and baseline values obtained from linear regression analysis applied to data of the type shown in FIG. 4 (though, of course, collected from human patients). Exemplary calibration techniques for determining the conversion factors based on a linear equation derived from linear regression are discussed below. At step 104, the pacer/ICD then estimates LAP or other cardiac pressure values within the patient by applying the conversion factors retrieved from memory to the measured time delays or by using a neural network, linear discriminant analyzer (LDA) or other appropriate technique. Also, the pacer/ICD may classify the pressure value within discrete intervals, such as LOW, MEDIUM and HIGH. That is, the pacer/ICD need not calculate specific values of the cardiac pressure but may instead simply determine whether the pressure is low, medium or higher, or within other predetermined ranges. The discrete intervals may be used as part of a prediction model that predicts LAP trends in a discrete fashion.

When using slope and baseline conversion factors to estimate specific values of pressure, cardiac pressure may be generally estimated using:

$$\text{Cardiac Pressure} = \text{Delay} * \text{Slope} + \text{Baseline}$$

where Delay represents the measured conduction delay, i.e. LV-RV delay, etc., and Slope and Baseline represent the conversion factors appropriate for use with the particular delay. This formula assumes a linear relationship between cardiac pressure and the measured conduction delay, which is an appropriate presumption based on the particular conduction delays discussed herein, at least insofar as estimating LAP is concerned. Routine experimentation may be performed to determine whether a linear relationship is also suitable for use in estimating other particular cardiac chamber values, such as LVP, LV EDV or LV EDP, or is also suitable for use with other conduction delays, such as RA-LV, RA-RV, RA-LA, etc. Moreover, it should be understood that linear models need not necessarily be used, i.e. more sophisticated correlation models may instead by employed. Linear models are preferred in view of their simplicity. As noted, neural networks or LDAs may instead be employed, where appropriate.

At step 106, the pacer/ICD then adaptively adjusts pacing timing parameters in a closed loop to improve LAP or other cardiac performance values. For example, LV-RV delays or AV delays may be adjusted in an effort to reduce LAP. That is, a combination of AV delay and LV-RV delay values are selected that yield the lowest LAP values. However, other delay parameters may be adjusted as well, such as inter-atrial delays or, if the implantable system is equipped to pace at two or more locations within a given atrial or ventricular chamber, then intra-atrial or intraventricular delays may be adjusted. Adaptive adjustment techniques are discussed in greater detail below. At step 108, the pacer/ICD tracks CHF, controls pacing therapy (such as CRT), generates warnings and/or stores diagnostic information based on estimated LAP values or other estimated cardiac chamber parameters. As already explained, the warnings and/or diagnostic data can be forwarded to a physician for review. Preferably, the diagnostic data includes the estimated LAP values for physician review. This is particularly advantageous since physicians are typically more comfortable reviewing LAP information than raw conduction delay values.

Preferably, steps 100-108 are repeated for each heartbeat to track changes in LAP on a beat-by-beat basis, adjust pacing parameters, track CHF, etc. That is, in some implementations, a near real-time LAP(t) function may be estimated so as to allow the pacer/ICD to track beat-to-beat changes in LAP.

This allows the pacer/ICD to respond promptly to changes within the heart of the patient. Also, the beat-by-beat LAP estimates may be applied to a predictor or prediction model so as to predict changes in LAP so that therapy may be controlled in advance of unacceptably high LAP levels or so that warnings may be generated in advance.

If the LV and RV are both being paced so that interventricular conduction delays are not readily measurable via IEGMS, the pacer/ICD may be programmed to periodically suspend RV pacing (or LV pacing) so as to permit at least a few intrinsic ventricular depolarizations so that the conduction delays can be measured. Alternatively, the electrical conduction delay technique of the invention may be used in conjunction with impedance-based mechanical delay techniques, which can derive estimates of LAP during those heartbeats when LV-RV conduction delays are not readily measurable. See, for example, U.S. patent application Ser. No. 11/558,194, by Panescu et al., cited above. In general, the conduction delay-based LAP estimation techniques of the invention can be combined with a variety of other LAP estimation techniques to derive a final estimate of LAP. Still further impedance signals may be analyzed to determine the electrical conduction delays from which cardiac pressure may then be estimated using appropriate conversion factors. In this regard, it is known in the art that electrical impedance changes may be indicative of changes in heart chamber dimensions. See, e.g., U.S. Pat. No. 5,003,976 to Alt. Alt describes that analyzing the impedance between two intracardiac electrodes may be used to determine changes in cardiac chamber volumes. As already explained, changes in chamber volume also affect conduction delays, allowing impedance signals to be used to detect conduction delays, particularly in circumstance where such delays cannot readily be determined from IEGMs.

Although the examples described herein are primarily directed to estimating LAP, other cardiac performance parameters may alternatively be estimated, such as LV EDV, LV EDP, RVP, RAP, etc., by using appropriate conversion factors in combination with appropriate conduction delays. Otherwise routine experimentation may be performed to identify particular parameters detectable using the techniques of the invention and the appropriate conduction delays and conversion factors. In some cases, a linear conversion may not be suitable and algorithms that are more sophisticated may be required to convert conduction delays into parameter estimates. In some cases, multiple conduction delays may be required to properly estimate a particular parameter. That is, multiple conduction delays may be measured using different electrodes so as to permit the pacer/ICD to estimate chamber pressures and volumes within different chambers of the heart, assuming appropriate conversion values have been determined and calibrated. To this end, the implanted system may be equipped, e.g., with multiple electrodes per lead or with multiple leads per chamber. Unipolar, bipolar or cross-chamber sensing systems may be employed, where appropriate.

Turning now to FIGS. 5-13, various illustrative embodiments will be described in greater detail.

Exemplary LAP Estimation Techniques

Figure 5:
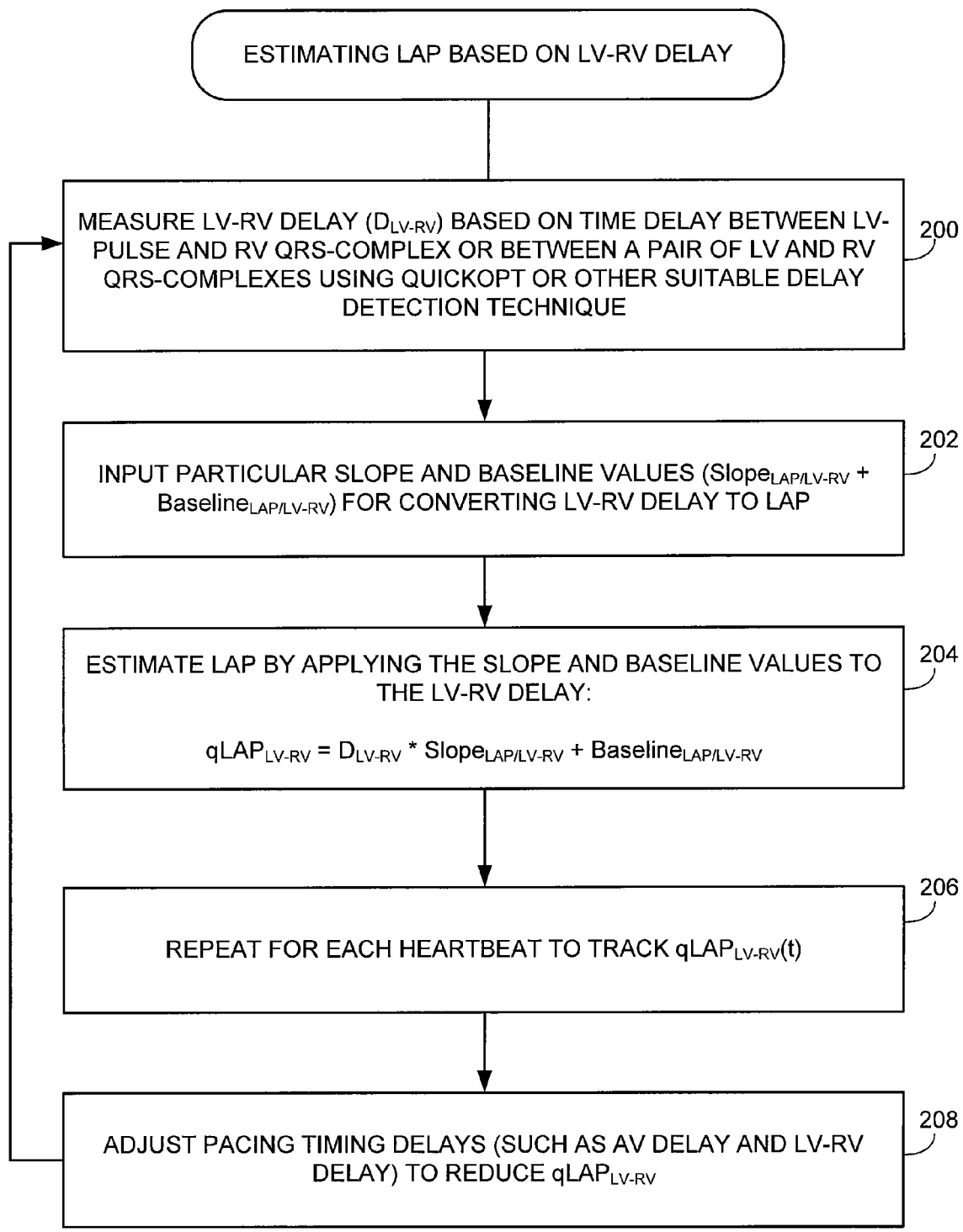
FIG. 5 is a flow diagram illustrating a particular example of the illustrative technique of FIG. 3 wherein LAP is estimated based on measured LV-RV delays, along with appropriate slope and baseline calibration values, to produce a qLAP value.

FIG. 5 provides an LV-RV delay-based LAP detection example wherein QuickOpt procedures for ascertaining the conduction delays. At step 200, the pacer/ICD measures the LV-RV delay ($D_{LV-RV}$) based on time delay between an LV-pulse and an RV QRS-complex or between a pair of LV and RV QRS-complexes using QuickOpt or other suitable delay detection technique. The QuickOpt technique is discussed in U.S. Patent Application No. 2005/0125041, cited above. For the sake of completeness, pertinent portions of the QuickOpt code are provided in the attached appendix (Appendix A). The example of Appendix A primarily operates to set RV thresholds. However, the LV-RV delay may be obtained using information generated by the code. That is, in the code, "ndx_lv" is the location of the LV QRS. "ndx_rv" is the location of the RV QRS. Hence, the LV-RV delay may be obtained by subtracting ndx_rv from ndx_lv (or vice versa).

At step 202, the pacer/ICD inputs the particular slope and baseline values ($Slope_{LAP/LV-RV}$ and $Baseline_{AP/LV-RV}$) for converting the delay value ($D_{LV-RV}$) into an estimate of LAP (denoted $qLAP_{LV-RV}$). The slope and baseline values (which also may be referred to as gain and offset values) are predetermined conversion values that the pacer/ICD retrieves from memory. Calibration techniques for initially deriving the conversion values will be discussed below with reference to FIGS. 8-13. At step 204, the pacer/ICD estimates LAP by applying the slope and baseline values to the delay value:

$$qLAP_{LV-RV} = D_{LV-RV} * Slope_{LAP/LV-RV} + Baseline_{LAP/LV-RV}$$

As indicated by step 206, the pacer/ICD repeats for each heartbeat to track qLAP(t). The LV-RV subscript is applied to qLAP to indicate that this estimate is made based on LV-RV delays (rather than some other conduction delay value.) The LAP/LV-RV subscript is applied to Slope and Baseline to indicate that these conversion factors are appropriate for use in estimating LAP based on LV-RV delays (rather than some other cardiac chamber parameter estimated from some other conduction delay value.)

Figure 6:
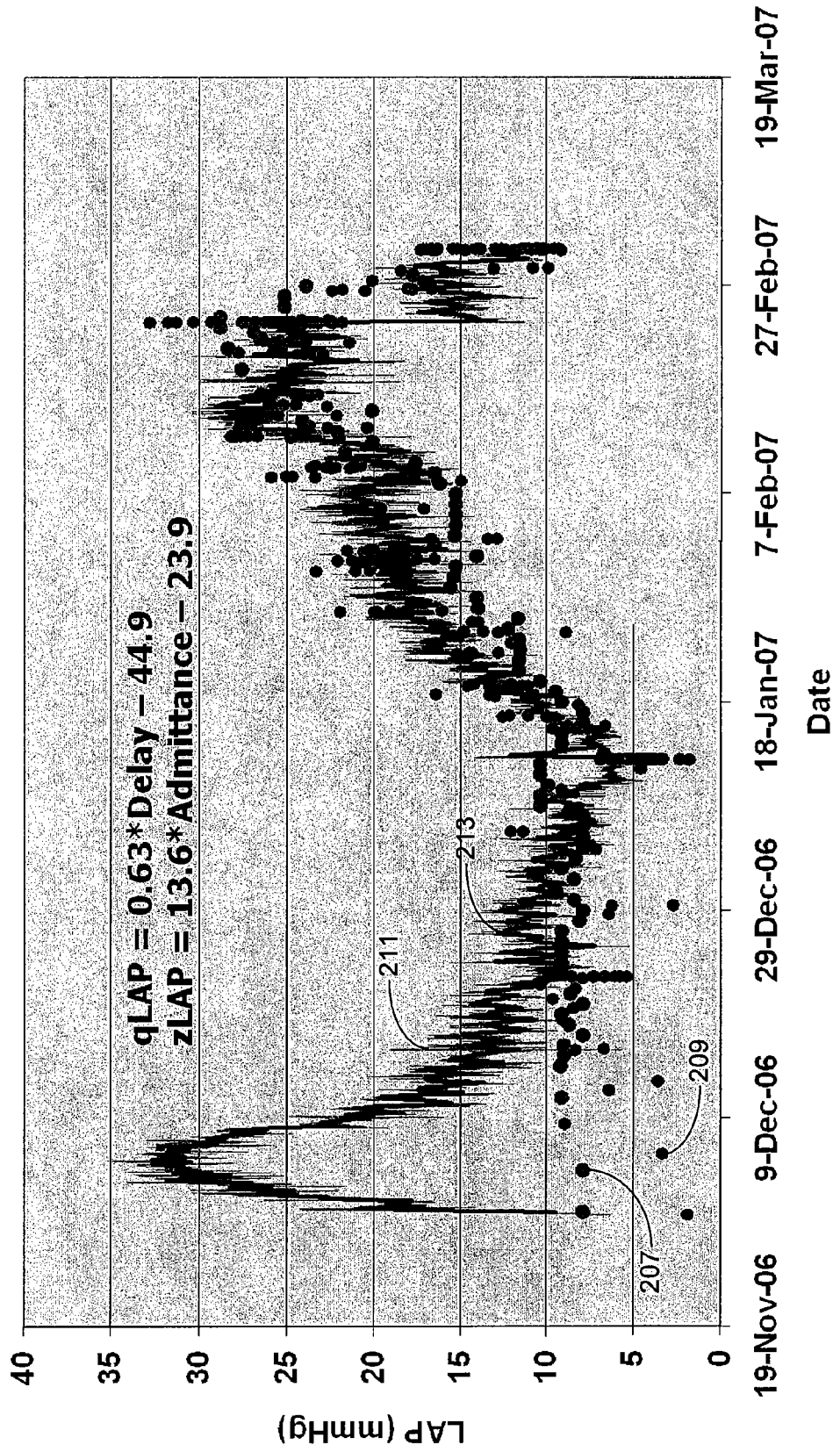
FIG. 6 is a graph providing exemplary data illustrating changes over time in qLAP values estimated within a canine test subject using the technique of FIG. 5.

FIG. 6 illustrates $qLAP_{LV-RV}$ values obtained within the same canine test subject of FIG. 4 showing changes over time as heart failure is induced. Light-shaded dots 207 are $qLAP_{LV-RV}$ values calculated as described herein. The darker-shaded dots 209 are actual LAP values measured using the HeartPOD system, discussed above, which includes an LAP sensor. As can be seen, the $qLAP_{LV-RV}$ values correlate fairly well with the HeartPOD values, verifying that the estimation is effective. (The $qLAP_{LV-RV}$ values are not necessarily identical to the actual LAP values since $qLAP_{LV-RV}$ merely provides an estimate of LAP and not a precise value.) The graph also shows zLAP values (represented by way of the light-shaded curve 211), as well as a six point moving average of ZLAP (represented by way of the dark-shaded curve 213). The ZLAP values were obtained using the impedance-based LAP estimation detection techniques set forth in U.S. patent application Ser. No. 11/559,235, cited above. (More generally, the techniques described therein are "admittance-based.") As can be seen, the zLAP estimates diverge from $qLAP_{LV-RV}$ values and from the true LAP values during the first couple of weeks of data. This is due to healing in and around the recently implanted electrodes, which affects impedance measurements. Hence, one advantage of the conduction delay-based techniques described herein (i.e. qLAP techniques) is that reliable estimates can be achieved even during the first few weeks following lead implant. (Note that the figure also provides the slope and baseline values used in calculating ZLAP (based on admittance) and $qLAP_{LV-RV}$ (based on the LV-RV conduction delay).)

Returning to FIG. 5, at step 208, the pacer/ICD adjusts the timing delays (such as the LV-RV and AV delays) in an effort reduce $qLAP_{LV-RV}$ so as to mitigate CHF or other heart ailments. In this regard, the various pacing timing parameters noted above may be adaptively adjusted. That is, typically, at least the AV and LV-RV timing parameters are adjusted. Advantageously, the direction and magnitude of the adjustment need not be known in advance. Rather, the pacer/ICD makes an incremental adjustment in one timing parameter in one direction, then determines whether the adjustment improved $qLAP_{LV-RV}$ or not. If an improvement is gained, the pacer/ICD makes an additional incremental adjustment in that timing parameter in that same direction in an attempt to achieve still further improvement. If the adjustment has an adverse effect on $qLAP_{LV-RV}$, the pacer/ICD makes an incremental adjustment in the same timing parameter but in the opposite direction in an attempt to achieve an improvement in $qLAP_{LV-RV}$. The magnitudes of the adjustments are adaptively varied so as to further optimize the parameter. If the initial adjustment had no effect, the pacer/ICD selects a different timing parameter to adjust. Once a particular parameter is optimized, the pacer/ICD can select a different parameter. For example, once AV delay has been optimized, the VV pacing delay may then be optimized. The range within which the parameters are automatically adjusted can be restricted via device programming to ensure that the parameters remain within acceptable bounds.

Care should be taken when optimizing or adapting pacing parameters when the parameter that is to be optimized is the parameter that is initially measured and used to estimate qLAP. Such closed loop feedback techniques are not precluded but it is often appropriate to restrict the range through which the parameters are automatically adjusted or by providing other suitable feedback control techniques. For example, insofar as optimizing or adapting VV delays based on qLAP values derived from LV-RV delays are concerned, the VV delay may be adjusted from a qLAP value estimated based on LV-RV delays by defining suitable adjustment criteria. This is generally equivalent to a closed loop system where the feedback variable is optimized to a pre-established criterion (e.g. by keeping qLAP to less than 25 mmHg.). This is discussed more fully below. Similarly, qLAP could be used to adjust pacing sites to reach a pre-established estimated LAP goal.

Figure 7:
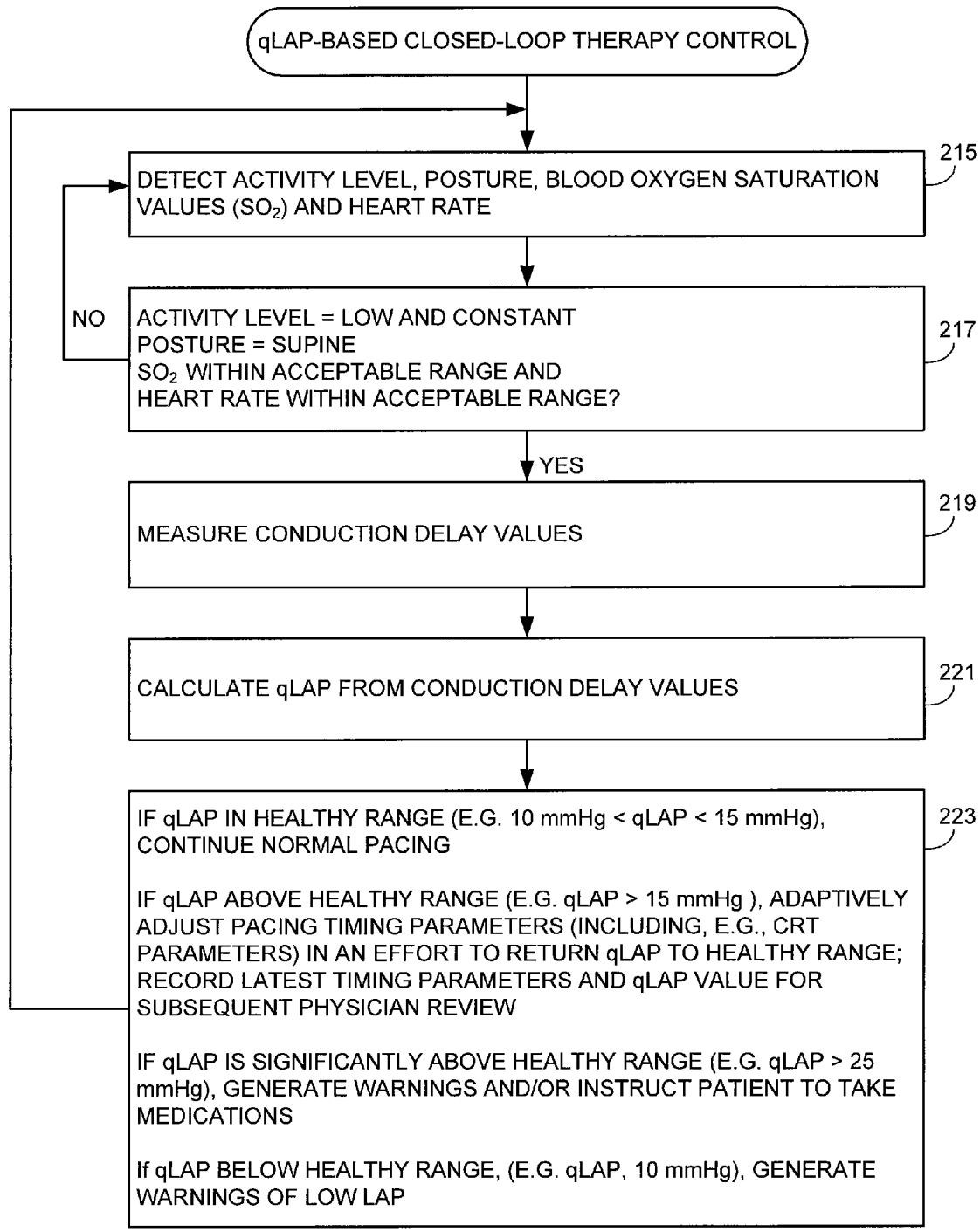
FIG. 7 is a flow diagram illustrating a closed-loop procedure for adaptively adjusting pacing parameters based on estimated cardiac pressure values obtained in accordance with the exemplary estimation technique of FIG. 5.

FIG. 7 provides an exemplary closed-loop adjustment procedure wherein pacing parameters are adaptively adjusted so as to reduce a qLAP but only under certain conditions. Beginning at step 215, the pacer/ICD detects detect patient activity level, patient posture, blood oxygen saturation values ($SO_2$) and heart rate. Patient activity may be detected using an accelerometer or other physical activity sensor mounted within the pacer/ICD itself or positioned elsewhere within the patient. Depending upon the implementation, the physical activity sensor may be employed in conjunction with an "activity variance" sensor, which monitors the activity sensor diurnally to detect the low variance in the measurement corresponding to a rest state. For a complete description of an activity variance sensor, see U.S. Pat. No. 5,476,483 to Bornzin et al., entitled "System and Method for Modulating the Base Rate during Sleep for a Rate-Responsive Cardiac Pacemaker." Techniques for detecting patient posture or changes in posture are set forth in U.S. patent application Ser. No. 10/329,233, of Koh et al., entitled "System and Method for Determining Patient Posture Based On 3-D Trajectory Using an Implantable Medical Device". Other techniques are set forth in U.S. Pat. No. 6,044,297 to Sheldon, et al. "Posture and Device Orientation and Calibration for Implantable Medical Devices." Techniques for detecting $SO_2$ are described in U.S. Pat. No. 5,676,141 to Hollub, entitled "Electronic Processor for Pulse Oximeters." Depending upon the particular application, either arterial $SO_2$ (i.e. $SaO_2$), or venous $SO_2$ (i.e. $SvO_2$), or both, may be detected and exploited. Heart rate may be derived from an IEGM.

At step 217, the pacer/ICD determines whether all of the following are true: (1) the patient is at rest and has been at rest for some predetermined amount of time, based on patient activity; (2) the posture is supine; (3) $SO_2$ is within an acceptable predetermined range consistent with patient rest; and (4) heart rate is within an acceptable predetermined range consistent with rest (such as a heart rate below 80 beats per minute (bpm)). If these conditions are met, the pacer/ICD proceeds to steps 219-223 to adaptively adjusting the pacing parameters. That is, at step 219, the pacer/ICD measures conduction delay values, such as LV-RV delays. At step 221, the pacer/ICD calculates qLAP from the measured delay using the techniques discussed above. At step 223, the pacer/ICD adaptively adjusts pacing parameters such as CRT timing parameters in an effort to maintain qLAP within a predetermined acceptable range and also records the latest timing parameters and qLAP values for subsequent physician review. For example, the pacer/ICD may be programmed to attempt to maintain qLAP within the range of 10-15 mmHg. In one example, if qLAP is initially found to be within that range, no pacing parameter adjustments are made. However, if qLAP is found to be in the range of 15-25 mmHg, then CRT parameter are adjusted in an attempt to reduce qLAP to within 10-15 mmHg. If qLAP is found to exceed 25 mmHg, then the pacer/ICD may be programmed to warning the patient (and/or the appropriate medical personal) and/or to initiate appropriate therapy. For example, if a drug pump is provided, the pacer/ICD may control the drug pump to deliver diuretics or other medications directed to reducing LAP (assuming such medications are available and have been found to be safe and effective for delivery via an implantable drug pump.) If no drug pump is provided, the pacer/ICD may relay instruction signals to the patient (and/or appropriate medical personnel) to direct the patient to take suitable medications. In this manner, medications directed to reducing LAP may be titrated. Alternatively, warnings may simply be generated that direct the patient to see his or her physician. The following summarizes one exemplary implementation of these strategies:

If qLAP in healthy range (e.g. 10 mmHg<qLAP<15 mmHg), continue normal pacing

If qLAP above healthy range (e.g. qLAP>15 mmHg), adaptively adjust pacing timing parameters (including, e.g., CRT parameters) in an effort to return qLAP to healthy range; record latest timing parameters and qLAP value for subsequent physician review If qLAP is significantly above healthy range (e.g. qLAP>25 mmHg), generate warnings and/or instruct patient to take medications If qLAP below healthy range, (e.g. qLAP, 10 mmHg), generate warnings of low LAP Still further, any CRT adjustments may be made based not only on qLAP but on other parameters as well. For example, adjustments may be made so as to maintain qLAP within a given range while also maintaining certain IEGM morphological parameters (such as P-wave width) within a certain range. As can be appreciated a wide range of feedback strategies and techniques may be exploited.

Processing then returns to step 215 and, so long as the conditions of step 217 are still met, the pacer/ICD will continually and incrementally adjust the pacing parameters using the adaptive procedure. This helps ensure that adjustments are made while the patient is in a particular resting state so that changes to qLAP due to factors other than the changes in the pacing parameters (such as patient activity) will not adversely affect the adaptive procedure. By looking at just qLAP values, which can be calculated fairly quickly, the procedure can typically be performed in near real-time. Once the patient becomes active again, further adaptive adjustments to pacing parameters are suspended until the patient is again at rest. Note that the list of patient status conditions in step 217 is merely exemplary. In other examples, more or fewer conditions may be used. For example, in other implementations, the patient need not necessarily be supine. Also, if the patient is subject to AF, the acceptable heart rate range may be expanded or that condition eliminated entirely so that frequent episodes of AF do not prevent adaptive adjustment of the pacing parameters.

Various additional techniques and strategies for adaptively optimizing pacing parameters may be employed, where appropriate, to supplement or enhance the techniques described herein. Examples are set forth in U.S. patent application Ser. No. 11/231,081, filed Sep. 19, 2005, of Turcott, entitled "Rapid Optimization of Pacing Parameters"; U.S. patent application Ser. No. 11/199,619, filed Aug. 8, 2005, of Gill et al, entitled "AV Optimization Using Intracardiac Electrogram"; U.S. patent application Ser. No. 11/366,930, of Mulleretal., filed Mar. 1, 2006, entitled "System and Method for Determining Atrioventricular Pacing Delay based on Atrial Repolarization"; U.S. patent application Ser. No. 10/928,586, of Bruhns et al., entitled "System and Method for Determining Optimal Atrioventricular Delay based on Intrinsic Conduction Delays", filed Aug. 27, 2004; and U.S. Pat. No. 6,522,923 to Turcott, entitled "Methods, Systems and Devices for Optimizing Cardiac Pacing Parameters Using Evolutionary Algorithms." See, also, the adaptive adjustment techniques described in the above-cited patent application of Panescu et al. (Ser. No. 11/558,194).

The locations of pacing sites may also be adaptively adjusted based on qLAP. In one particular example, the pacer/ICD is equipped with N electrodes in the RV, where N is an arbitrary number of electrodes. The pacer/ICD calculates qLAP when unipolar pacing is performed using each RV electrode, i.e. $RV_1$—case, $RV_2$—case, $RV_3$—case, etc. The pacer/ICD then selects the particular RV electrode that achieves the lowest value of qLAP for use in performing further pacing. Once optimal pacing sites are chosen, CRT timing parameters may be optimized using the techniques above for use with that particular pacing site. Similarly, the LV lead may carry multiple CRT pacing electrodes. In a similar fashion, optimal pacing configurations can be selected from the electrodes on the LV lead. Yet similarly, combined RV and LV pacing configurations may be selected to reduce qLAR Alternatively, all these pacing electrodes can be separately, or individually, distributed on endocardial, epicardial or within myocardial tissue. The electrodes can be carried on separate leads, on multiple leads or implanted individually. Note that, whenever switching between pacing electrodes, new conversion factors will need to be applied/available. Accordingly, the pacer/ICD will need to have sufficient resources to store the many conversion factors and to keep track of which ones are well calibrated and which ones are inaccurate (or otherwise not useable).

Calibration Techniques

Figure 8:
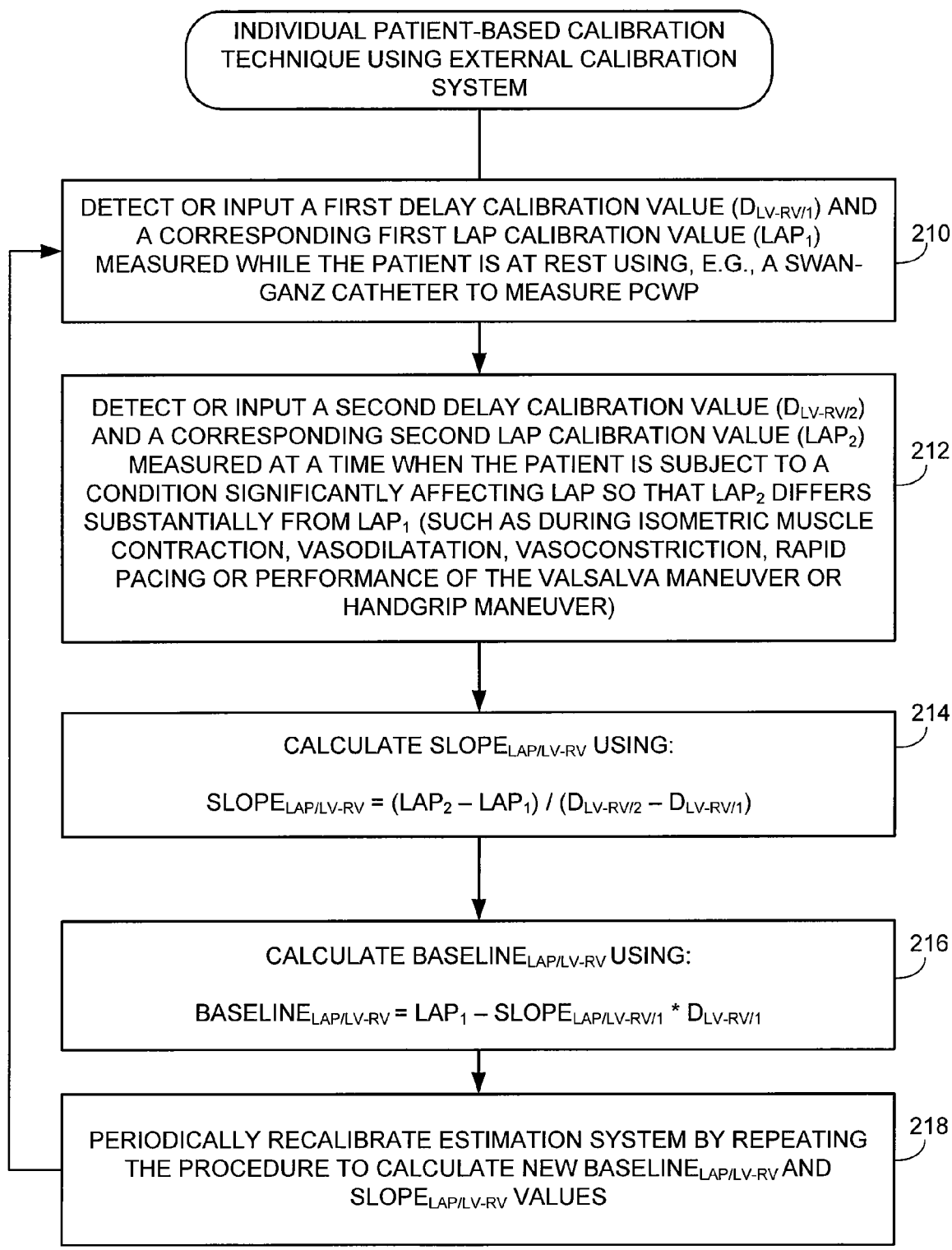
FIG. 8 is a flow diagram illustrating an exemplary procedure for calibrating the LV-RV delay-based LAP estimation technique of FIG. 5 using calibration parameters obtained within the patient in which the system is implanted.

A variety of techniques may be used to initially determine and subsequently adjust the conversion values (Slope$_{LAP/LV-RV}$ and Baseline$_{LAP/LV-RV}$), i.e. to calibrate the delay-based estimation technique of FIG. 5. FIG. 8 summarizes a technique wherein calibration is performed based on calibration values obtained within the particular patient in which the pacer/ICD is implanted. That is, the conversion values are optimized for use with the particular patient. The procedure of FIG. 8 is performed by a physician during the implant procedure of the pacer/ICD while venous access is readily available and a Swan-Ganz catheter can be easily inserted. The procedure in FIG. 8 may be repeated or performed alternatively at a follow-up session after implantation of the pacer/ICD. At step 210, an external calibration system (such as the external programmer of FIG. 15) detects or inputs a first delay calibration value ($D_{LV-RV/1}$) and a corresponding first LAP calibration value ($LAP_1$) measured while the patient is at rest. Preferably, the delay value ($D_{LV-RV/1}$) is detected by the pacer/ICD itself using its leads and its internal detection circuitry, then transmitted to the external system. Simultaneously, $LAP_1$ is detected using, e.g., a Swan-Ganz catheter to measure PCWP. The LAP value is also relayed to the external programmer.

At step 212, detects a second delay calibration value ($D_{LV-RV/1}$) and a corresponding second LAP calibration value ($LAP_2$) measured at a time when the patient is subject to a condition significantly affecting LAP so that $LAP_2$ differs substantially from $LAP_1$. For example, the physician may have the patient perform isometric muscle contractions, particular using thoracic muscles, so as to change LAP within the patient. Alternatively, the physician may administer vasodilatation or vasoconstriction medications, so as to change LAP, or may temporarily reprogram the pacer/ICD to perform rapid pacing, which also changes LAP. Still further, the physician may have the patient perform the Valsalva maneuver, which reduces effective LAP secondary to reduced venous return, or may instead have the patient perform the handgrip maneuver, which tends to increase LAP. (The Valsalva maneuver occurs when a patient forcibly exhales for about 15 seconds against a fixed resistance with a closed glottis while contracting the abdominal muscles. A sudden transient increase in intra-thoracic and intra-abdominal pressures occurs, which tends to empty the chambers of the heart of blood, such that within 1 to 2 seconds (phase I of the Valsalva maneuver) the effective right atrial and right ventricular pressures drop to zero, while following 5 seconds (Late phase II) the effective left atrial and left ventricular pressures tend to reach zero.) Again, the conduction delay value is detected by the pacer/ICD itself then transmitted to the external system.

Thus, after step 212, the external system has obtained at least two pairs of calibration values ($LAP_1$, $D_{LV-RV/1}$ and $LAP_2$, $D_{LV-RV/2}$) where the LAP values differ substantially from one another. Since the LV-RV conduction delay varies due to changes in LV chamber volume that correlate with changes in the LAP, the delay values likewise differ from one another, permitting reliable calculation of the slope and baseline values.

At step 214, the external system calculates Slope$_{LAP/LV-RV}$ using:

$$\text{Slope}_{LAP/LV-RV}=(LAP_2-LAP_1)/(D_{LV-RV/2}-D_{LV-RV/1}).$$

At step 216, the external system calculates Baseline$_{LAP/LV-RV}$ using:

$$\text{Baseline}_{LAP/LV-RV}=LAP_1-\text{Slope}_{LAP/LV-RV/1}*D_{LV-RV/1}$$

These values are then transmitted to the pacer/ICD for storage therein for use in estimating LAP based on newly detected delay values using the technique of FIG. 5. Preferably, qLAP values provided by the pacer/ICD are compared with LAP values detected using the Swan-Ganz catheter to verify that the estimation system of the pacer/ICD has been properly calibrated.

As noted, LV-RV conduction delays are not the only delays that might be used in estimating LAP or other cardiac pressure values. Hence, the first and second delay calibration values are also more generally referred to herein as $D_1$ and $D_2$. The external system calculates Slope using:

$$\text{Slope}=(\text{Pressure}_2-\text{Pressure}_1)/(D_2-D_1).$$

The external system calculates Baseline using:

$$\text{Baseline}=\text{Pressure}_1-\text{Slope}*D_1.$$

Figure 9:
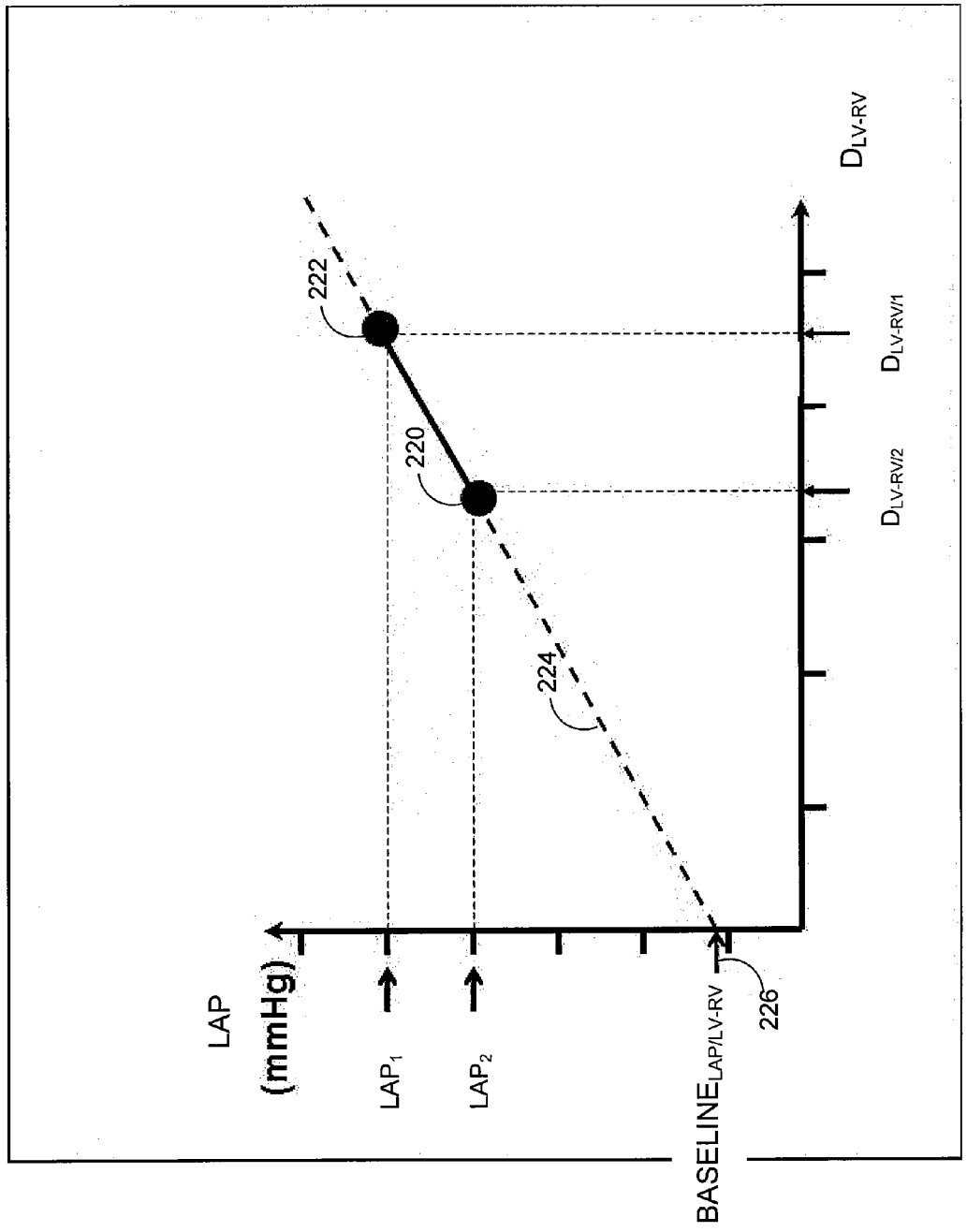
FIG. 9 is a graph illustrating a linear relationship between qLAP and LV-RV delay calibration values exploited by the calibration technique of FIG. 8.

FIG. 9 illustrates an exemplary pair of calibration values 220, 222, along with exemplary slope 224 and baseline values 226 derived therefrom using the technique of FIG. 8. Although only two pairs of calibration values are used in the example of FIG. 8, it should be understood that additional pairs of calibration values might be obtained. Linear regression techniques may be used to derive slope and baseline values from a plurality of pairs of calibration values. Also, as indicated by step 218, the recalibration procedure of FIG. 8 can be repeated periodically (such as during subsequent follow-up sessions with the patient) to update both the slope and baselines values to respond to changes, if any, that may arise within the patient, perhaps due to scarring near the sensing electrodes. Alternatively, a re-calibration technique may be performed by the pacer/ICD itself that re-calibrates only the baseline value. This is summarized in FIG. 10.

Figure 10:
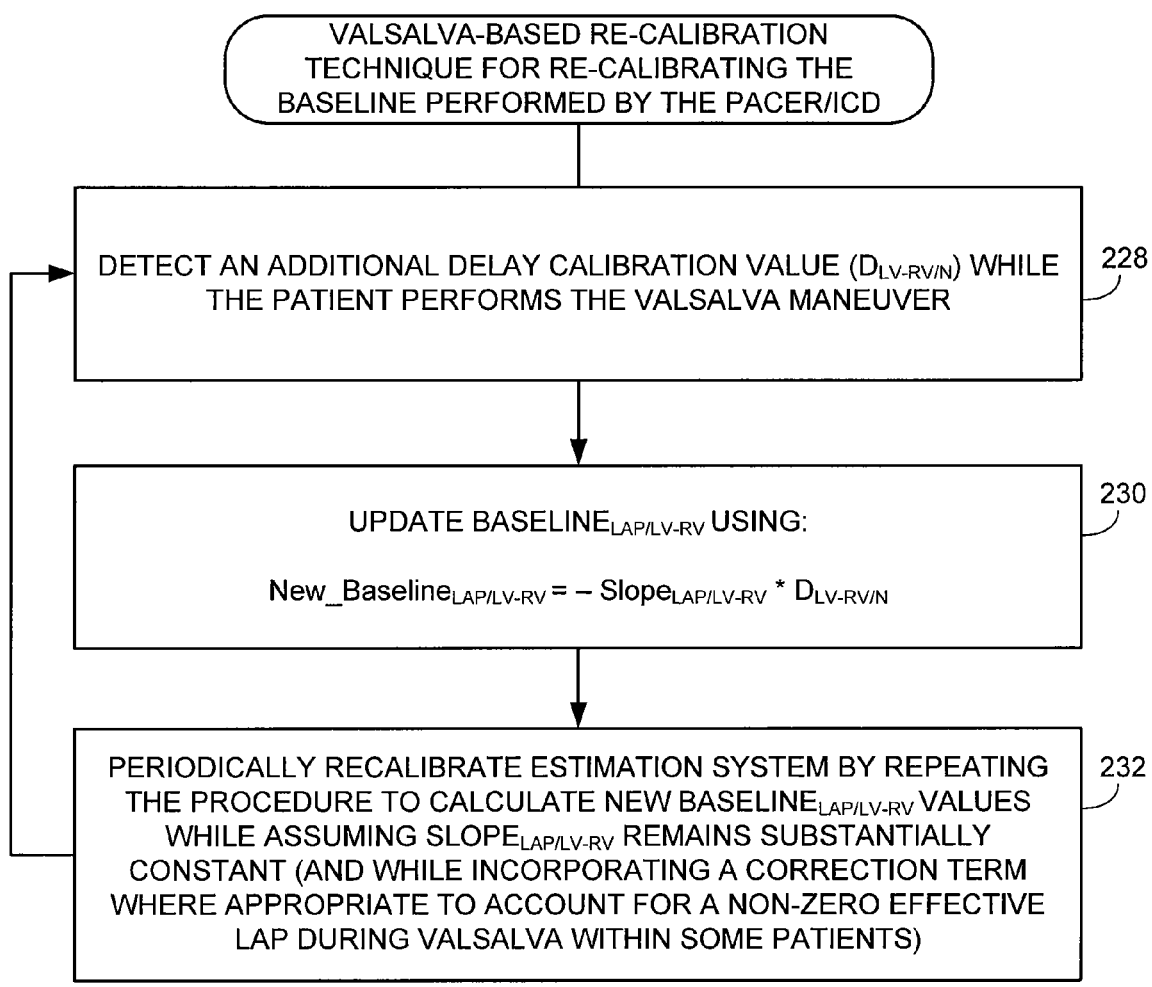
FIG. 10 is a flow diagram illustrating an exemplary procedure for re-calibrating the baseline value of the LV-RV delay-based LAP estimation technique of FIG. 5 using additional calibration parameters obtained within the patient while performing the Valsalva maneuver.

FIG. 10 illustrates a recalibration procedure performed by the pacer/ICD to re-calibrate the baseline value. The procedure exploits the assumption that the slope value, once calculated for a particular patient, typically does not change significantly within the patient. This allows the baseline value to be re-calibrated independently of the slope value. At step 228, the pacer/ICD detects an additional delay calibration value ($D_{LV-RV/N}$) while the patient performs the Valsalva maneuver. As already explained, during the Valsalva maneuver effective LAP drops to zero or near zero. Hence, a separate measurement of effective LAP is not required. Under the assumption that effective LAP drops to zero at the time when the additional delay value ($D_{LV-RV/N}$) is measured, the baseline value can be re-calculated, at step 230, based on the previous slope and the new delay value ($D_{LV-RV/N}$) using:

$$New\_Baseline_{LAP/LV-RV} = -Slope_{LAP/LV-RV} * D_{LV-RV/N}.$$

A particularly attractive feature of this recalibration procedure is that it is non-invasive and can be performed in the ambulatory setting in the physician's office during a routine follow-up visit. Preferably, re-calibration is performed while the patient is clinically stable.

In some patients with diastolic heart failure and poor left ventricular compliance who may have higher cardiac filling pressures (PCWP >20 mmHg) even when well compensated, the effective LAP may not drop completely to zero during a Valsalva maneuver and a correction term may need to be applied to account for this possibility. (See, for example, FIG. 5 of U.S. Patent Application 2004/0019285 of Eigler, et al., entitled "Apparatus for Minimally Invasive Calibration of Implanted Pressure Transducers," which is incorporated by reference herein in its entirety.)

In order to determine whether a particular patient requires such a correction term, a third measurement of the conduction delay ($D_3$) during the original calibration procedure FIG. 8 should be obtained while the patient is performing the Valsalva maneuver. This assumes that $D_1$ and $D_2$ were not obtained during a Valsalva maneuver. The correction term ($qLAP_{VALSALVA}$) is simply computed using:

$$qLAP_{VALSALVA} = D_3 * Slope_{LAP/LV-RV} + Baseline_{LAP/LV-RV}$$

wherein $qLAP_{VALSALVA}$ is an effective LAP pressure value. Ideally, if the blood volume inside the left atrium significantly decreases during the Valsalva maneuver, then $qLAP_{VALSALVA}$ will be near zero. Step 230 may alternatively be computed using:

$$New\_Baseline_{LAP/LV-RV} = qLAP_{VALSALVA} - Slope_{LAP/LV-RV} * D_N.$$

The response of intracardiac pressures to the Valsalva is discussed in McClean et al., "Noninvasive calibration of cardiac pressure transducers in patients with heart failure: An aid to implantable hemodynamic monitoring and therapeutic guidance", Journal of Cardiac Failure, Vol. 12 No. 7 2006, pp 568-576. It is described therein that during the Valsalva maneuver the effective PCWP reduces nearly to zero as described above. A similar observation was observed for other chambers of the heart. In particular, the effective residual pressure within a specific cardiac chamber ($P_{eff}$) was computed as the difference between the measured intracardiac pressure ($P_{intracardiac}$) and the simultaneous intrathoracic or airway pressure ($P_{airway}$) averaged over the time interval from 5 to 10 seconds after the initiation of the Valsalva maneuver (Late phase II). The effective intracardiac pressure ($P_{eff}$) is computed using:

$$P_{eff} = P_{intracardiac} - P_{airway}$$

where ($P_{airway}$) is detected, e.g., using an external pressure detection system. See, for example, the upper airway apparatus of FIG. 2 of U.S. Patent Application 2004/0019285 of Eigler, et al., cited above. Thus, in order to estimate the effective LAP ($LAP_{eff}$) during the Valsalva maneuver one may obtain this measurement directly by computing average of the difference between the PCWP and the simultaneous airway pressure over the interval from 5 to 10 seconds following the initiation of the Valsalva maneuver (late Phase II). This may be written more specifically as:

$$LAP_{eff} = PCWP - P_{airway}$$

and $LAP_{eff}$ may be used alternatively as the correction term described above.

The new baseline value is then used when converting additional conduction delay values to effective qLAP values (step 204 of FIG. 5.) As indicated by step 232, the pacer/ICD can periodically recalibrate its estimation system by repeating the procedure to calculate new $Baseline_{LAP/LV-RV}$ values while assuming $Slope_{LAP/LV-RV}$ remains substantially constant and using the correction term where appropriate.

In practice, the procedure of FIG. 10 may be initiated by periodically having the pacer/ICD transmit a signal to the bedside monitor providing instructions to the patient to perform the Valsalva maneuver. The pacer/ICD detects the new conduction delay value during the Valsalva maneuver and updates the baseline value. The pacer/ICD may be additionally programmed to verify that the patient actually performed the maneuver by, e.g., analyzing changes in respiration (as detected using otherwise conventional respiration detection techniques) to verify that respiratory patterns consistent with the Valsalva maneuver occur. The pacer/ICD can also time its detection of the additional conduction delay value based on the respiratory signals to help ensure that the new conduction delay value is measured at a point when effective LAP is expected to be zero. Alternatively, the re-calibration technique may be performed only under the supervision of a physician or other clinician during a follow-up session with the patient. Still, the re-calibration procedure eliminates the need to directly measure effective LAP during the follow-up using a Swan-Ganz catheter. The catheter is only employed during the original calibration procedure. Thus, FIG. 10 illustrates a technique wherein the baseline value is re-calibrated by the pacer/ICD under the assumption that slope does not change by exploiting the Valsalva maneuver. The Valsalva maneuver may also be exploited to re-calibrate both slope and baseline, if needed within a particular patient. This is illustrated in FIGS. 11 and 12.

Figure 11:
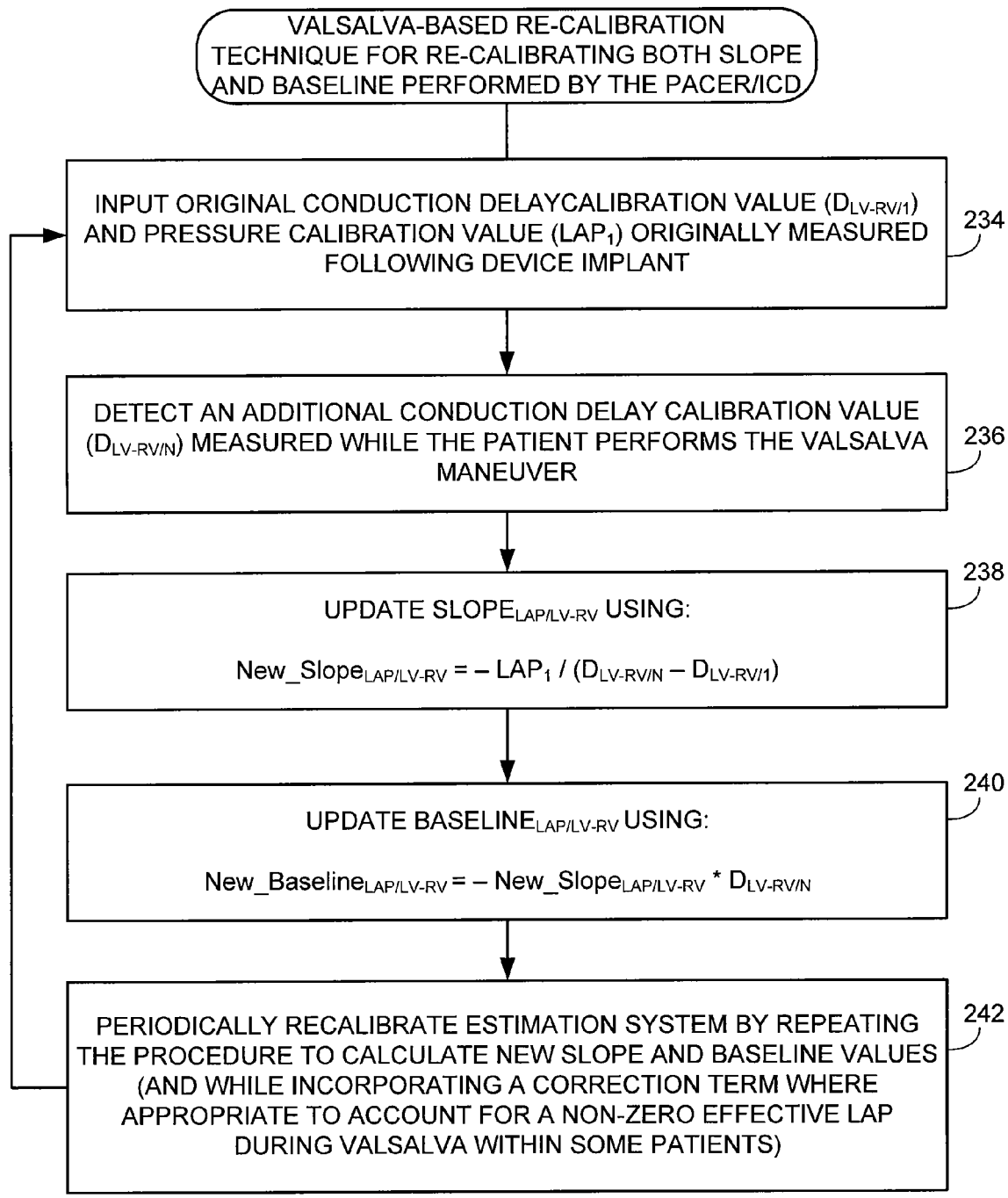
FIG. 11 is a flow diagram illustrating an exemplary procedure for re-calibrating both slope and baseline values of the LV-RV delay-based LAP estimation technique of FIG. 5 using additional calibration parameters obtained within the patient while performing the Valsalva maneuver.
Figure 12:
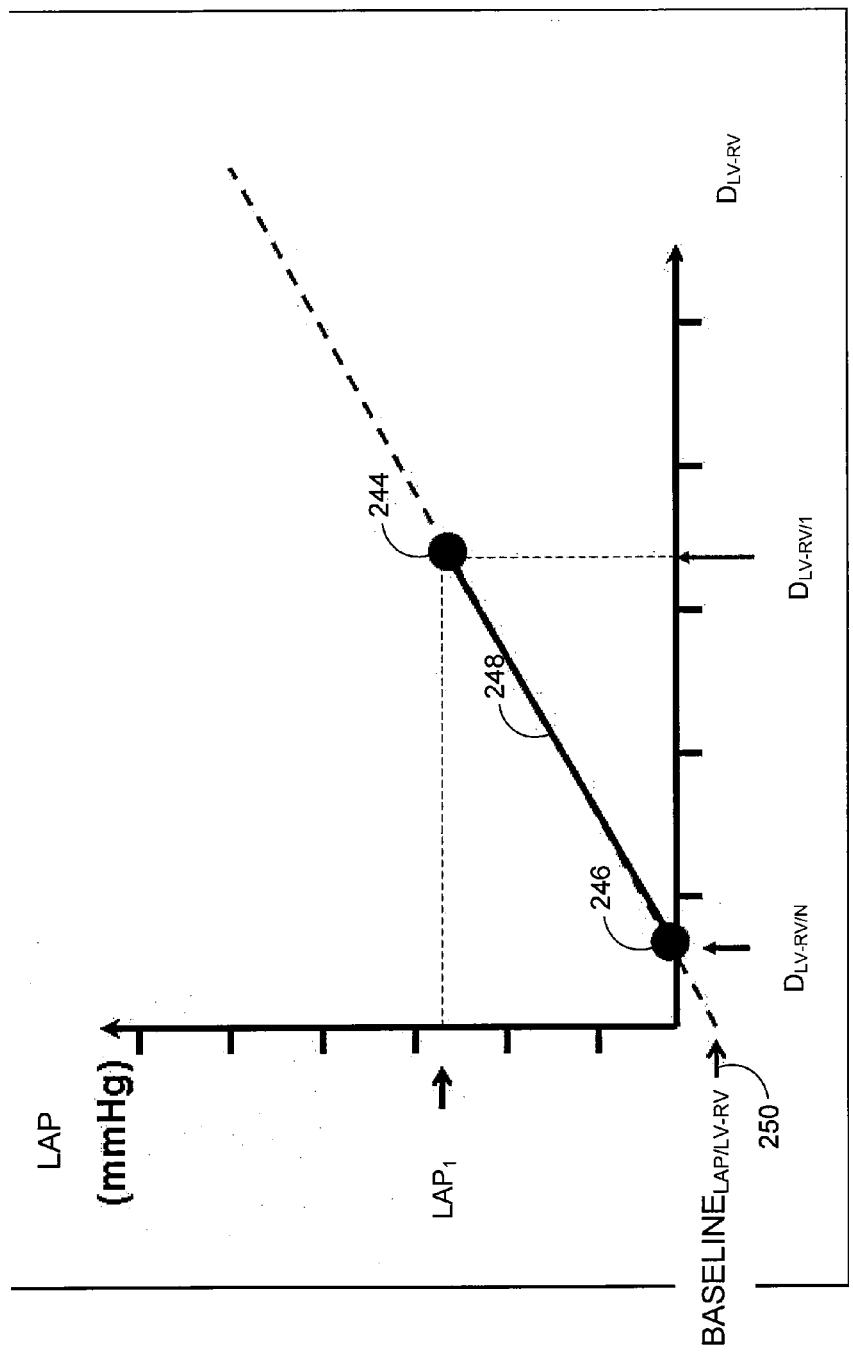
FIG. 12 is a graph illustrating a linear relationship between qLAP and LV-RV delay calibration values exploited by the re-calibration technique of FIG. 11, and, in particular, illustrating a zero LAP value obtained within the patient during the Valsalva maneuver.

FIG. 11 summarizes a recalibration procedure performed by the pacer/ICD to re-calibrate both the slope and baseline values. The procedure can be used in patients where the slope value changes. At step 234, the pacer/ICD inputs the original conduction delay calibration value ($D_{LV-RV/1}$) and effective pressure calibration value ($LAP_1$) originally measured following device implant (FIG. 8) or during a previous calibration procedure. The assumption is that $LAP_1$ is unchanged from the previous calibration procedure. At step 236, the pacer/ICD detects an additional conduction delay calibration value ($D_{LV-RV/N}$) while the patient performs the Valsalva maneuver. As already noted, during the Valsalva maneuver effective LAP typically drops to at or near zero and so separate measurement of effective LAP is not required. Rather, it is assumed that effective LAP is zero when the additional conduction delay value ($D_{LV-RV/N}$) is measured, thus allowing the slope to be re-calculated, at step 238, using:

$$\text{New\_Slope}_{LAP/LV-RV} = -LAP_1/(D_{LV-RV/N} - D_{LV-RV/1}).$$

Once the new slope value is calculated, the new baseline value can be calculated, at step 240, using:

$$\text{New\_Baseline}_{LAP/LV-RV} = -\text{New\_Slope}_{LAP/LV-RV} * D_{LV-RV/N}.$$

More generally:

$$\text{Slope} = -\text{Pressure}_1/(D_N - D_1) \text{ and}$$

$$\text{Baseline} = -\text{Slope} * D_N.$$

The new slope and baseline values are then used when converting additional conduction delay values to effective qLAP values (step 206 of FIG. 5.) As indicated by step 242, the pacer/ICD can periodically recalibrate its estimation system by repeating the procedure to calculate new $\text{Baseline}_{LAP/LV-RV}$ and $\text{Slope}_{LAP/LV-RV}$ values and using the correction term where appropriate. As with the procedure of FIG. 10, the procedure of FIG. 11 may be initiated by periodically having the pacer/ICD transmit a signal to the bedside monitor providing instructions to the patient to perform the Valsalva maneuver or the procedure may be performed under the supervision of a physician or other clinician.

FIG. 12 illustrates an exemplary pair of calibration values 244, 246, along with exemplary slope 248 and baseline values 250 derived therefrom using the technique of FIG. 11. The first pair of calibration values 244 is obtained following implant. The second pair of calibration values 246 is obtained during the re-calibration procedure while the patient performs the Valsalva maneuver. Since the Valsalva maneuver is being performed, the effective LAP value of the second pair of calibration values 246 is zero and so the pressure need not be measured. The conduction delay value of the second pair along with the pressure and conduction delay values of the first pair are used to calculate the new slope 244 and baseline values 250 using the equations of FIG. 11.

Figure 13:
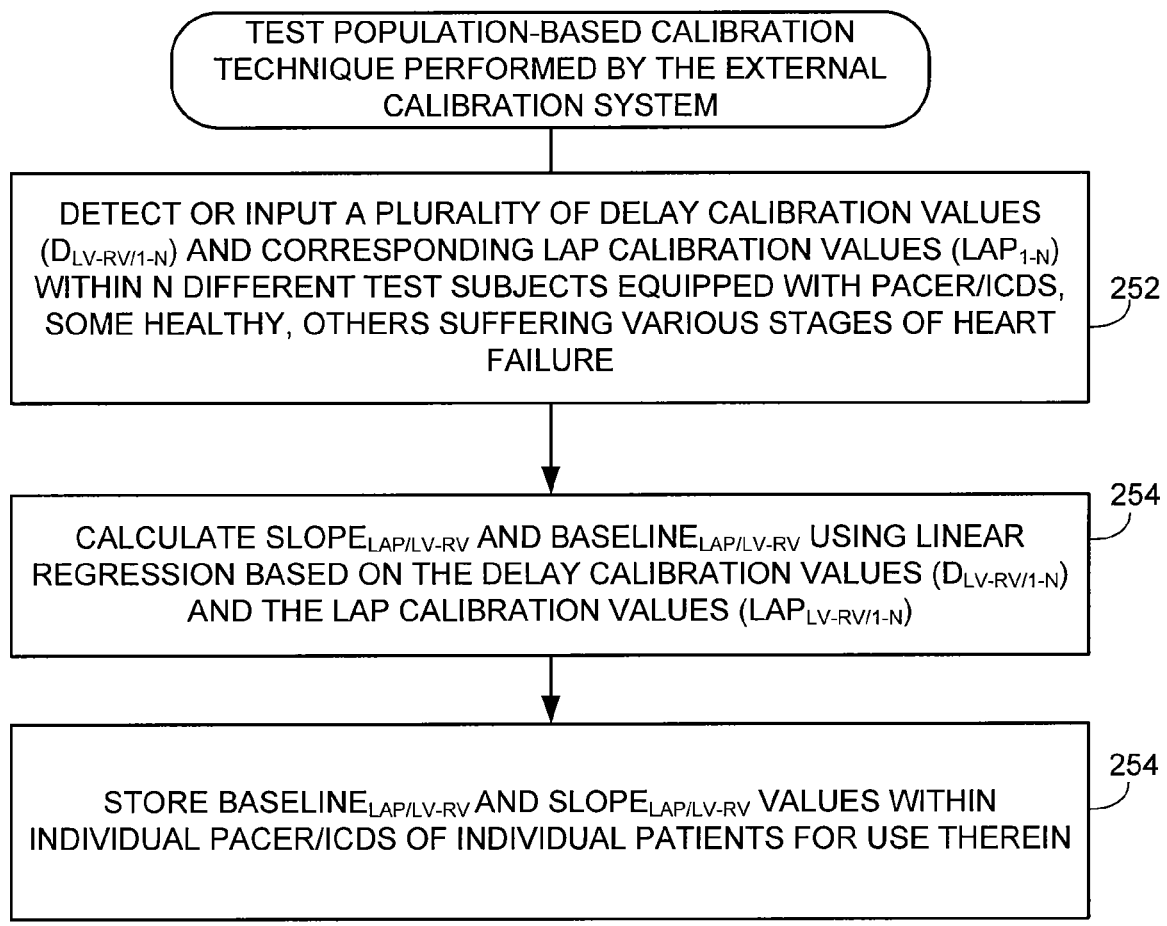
FIG. 13 is a flow diagram illustrating an exemplary procedure for calibrating the LAP-based technique of FIG. 5 using calibration parameters obtained from a population of test subjects.

Turning now to FIG. 13, techniques are summarized for calibrating or re-calibrating the conduction delay-based estimation procedure based on data from a population of human patients or human test subjects. In the specific example of FIG. 13, data is obtained from a plurality of test patients subject to various stages of heart failure and have various LAP values. Beginning at step 252, the external calibration system detects or inputs a plurality of conduction delay calibration values ($D_{LV-RV/1-N}$) and corresponding LAP calibration values ($LAP_{1-N}$) within N different human test subjects equipped with pacer/ICDs, some healthy, others suffering differing stages of heart failure, i.e. differing levels of severity of heart failure. The conduction delay values are detected by the pacer/ICDs of the test subjects, then relayed to the external calibration system. The LAP values may be obtained using Swan-Ganz catheters or the like. Since the test subjects exhibit differing stages of heart failure, differing values of LAP are thereby exhibited. At step 254, the external system then calculates $\text{Slope}_{LAP/LV-RV}$ and $\text{Baseline}_{LAP/LV-RV}$ values using linear regression based on the conduction delay calibration values ($D_{LV-RV/1-N}$) and the LAP calibration values ($LAP_{1-N}$). At step 256, the external system then stores the $\text{Slope}_{LAP/LV-RV}$ and $\text{Baseline}_{LAP/LV-RV}$ values within individual pacer/ICDs of individual patients for use therein. By obtaining data from a population of test subjects, the slope and baseline values are therefore likely to be effective within a wide range of patients. In some patients, these values may be sufficient to provide an adequate estimate of LAP. In other patients, these values may be used as starting points for further re-calibration. For example, the slope value obtained via the technique of FIG. 13 may be used within a wide range of patients along with patient-specific baseline values obtained using the baseline-only re-calibration procedure of FIG. 10.

Thus, a variety of techniques for calibrating the procedure, estimating LAP and then tracking heart failure are provided. These may be supplemented by using other non-conduction delay-based cardiac pressure detection and heart failure detection techniques. In some implementations, before an alarm is activated or any therapy is automatically delivered, the pacer/ICD employs at least one other detection technique to corroborate the detection of heart failure. Techniques for detecting or tracking heart failure are set forth the following patents and patent applications: U.S. Pat. No. 6,328,699 to Eigler, et al., entitled "Permanently Implantable System and Method for Detecting, Diagnosing and Treating Congestive Heart Failure"; U.S. Pat. No. 6,970,742 to Mann, et al., entitled "Method for Detecting, Diagnosing, and Treating Cardiovascular Disease"; U.S. Pat. No. 7,115,095 to Eigler, et al., entitled "Systems and Methods for Detecting, Diagnosing and Treating Congestive Heart Failure"; U.S. patent application Ser. No. 11/100,008, of Kil et al., entitled "System And Method For Detecting Heart Failure And Pulmonary Edema Based On Ventricular End-Diastolic Pressure Using An Implantable Medical Device", filed Apr. 5, 2005; U.S. patent application Ser. No. 11/014,276, of Min et al., entitled "System And Method For Predicting Heart Failure Based On Ventricular End-Diastolic Volume/Pressure Using An Implantable Medical Device", filed Dec. 15, 2004; U.S. patent application Ser. No. 10/810,437, of Bornzin et al., entitled "System and Method for Evaluating Heart Failure Based on Ventricular End-Diastolic Volume Using an Implantable Medical Device," filed Mar. 26, 2004 and U.S. patent application Ser. No. 10/346,809, of Min et al., entitled "System and Method for Monitoring Cardiac Function via Cardiac Sounds Using an Implantable Cardiac Stimulation Device," filed Jan. 17, 2003. See also: U.S. Pat. No. 6,572,557, to Tchou, et al., cited above. U.S. Pat. No. 6,645,153, to Kroll et al., entitled "System and Method for Evaluating Risk of Mortality Due To Congestive Heart Failure Using Physiologic Sensors", and U.S. Pat. No. 6,438,408 to Mulligan et al., entitled "Implantable Medical Device For Monitoring Congestive Heart Failure." Also, other calibration procedures may potentially be exploited in connection with the calibration techniques described herein. See, for example, U.S. Patent Application 2004/0019285 of Eigler, et al., cited above, particularly the various linear regression techniques discussed therein. Also, see the calibration procedures set forth in: U.S. patent application Ser. No. 11/559,235, by Panescu et al., entitled "System and Method for Estimating Cardiac Pressure Using Parameters Derived from Impedance Signals Detected by an Implantable Medical Device," cited above.

The examples above primarily pertain to estimating LV-RV delays. However, as already noted, other conduction delays can be used to estimate LAP. In general, any conduction delay that is affected by a particular cardiac pressure parameter might be exploited to estimate that cardiac pressure parameter. For example, LAP may also be estimated from AV delays. AV may be determined in much the same manner as LV-RV delays are determined (i.e. paced on pacer or sensed atrial and ventricular events.) Also, the morphology of the P-wave may be exploited to estimate AV delays (such as its shape or width). Typically, the wider the P-wave, the longer the AV delay. The narrower the P-wave, the shorter the AV delay. The morphology of atrial evoked responses may also be exploited to estimate AV delay. The QuickOpt code of the appendix may be modified as needed to provide these parameters. The following is a list of parameters that generally can be exploited to estimate LAP or other cardiac pressure parameter and which can be obtained from the QuickOpt code of the appendix or from modified versions thereof:

- A sense and A pace wave duration (indicates LA dilation and qLAP)
- V sense: RV-LV conduction delay
- RV pace-LV pace delay; LV-RV pace delay; or differences therebetween, including any appropriate correction terms.
- PR and AR: atrio-ventricular delays.
- RV-LV pace delay minus pacing latency (which is an alternative to V sense that tests for heart block in patients.)

Although primarily described with respect to examples having a pacer/ICD, other implantable medical devices may be equipped to exploit the techniques described herein. For the sake of completeness, an exemplary pacer/ICD will now be described, which includes components for performing the functions and steps already described. Also, an exemplary external programmer will be described, which includes components for performing the calibration steps already described.

Exemplary Pacer/ICD

Figure 15:
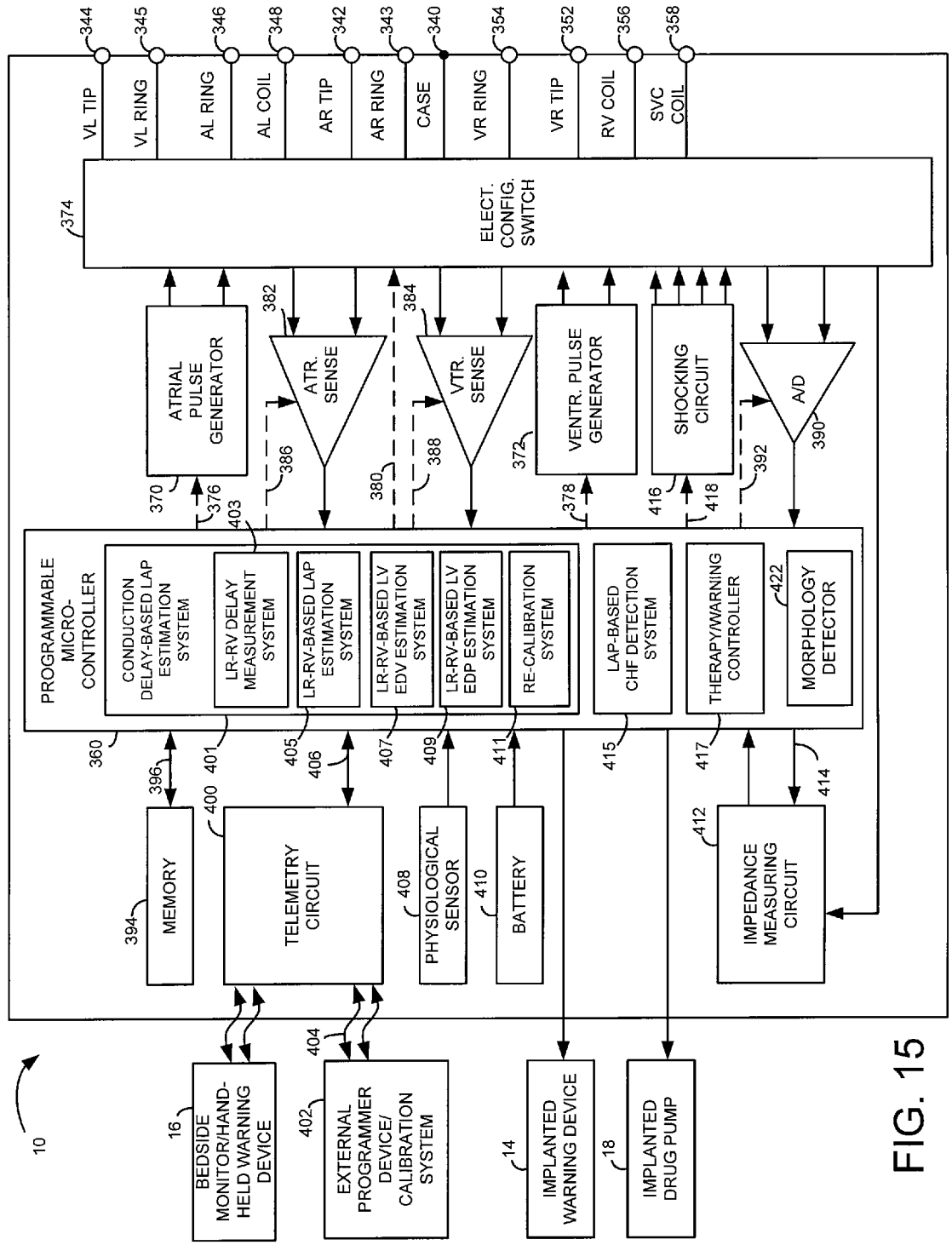
FIG. 15 a functional block diagram of the pacer/ICD of FIG. 14, illustrating basic circuit elements that provide cardioversion, defibrillation and/or pacing stimulation in the heart and particularly illustrating components for estimating LAP based on conduction delays and for adaptively adjusting pacing parameters in response thereto.
Figure 16:
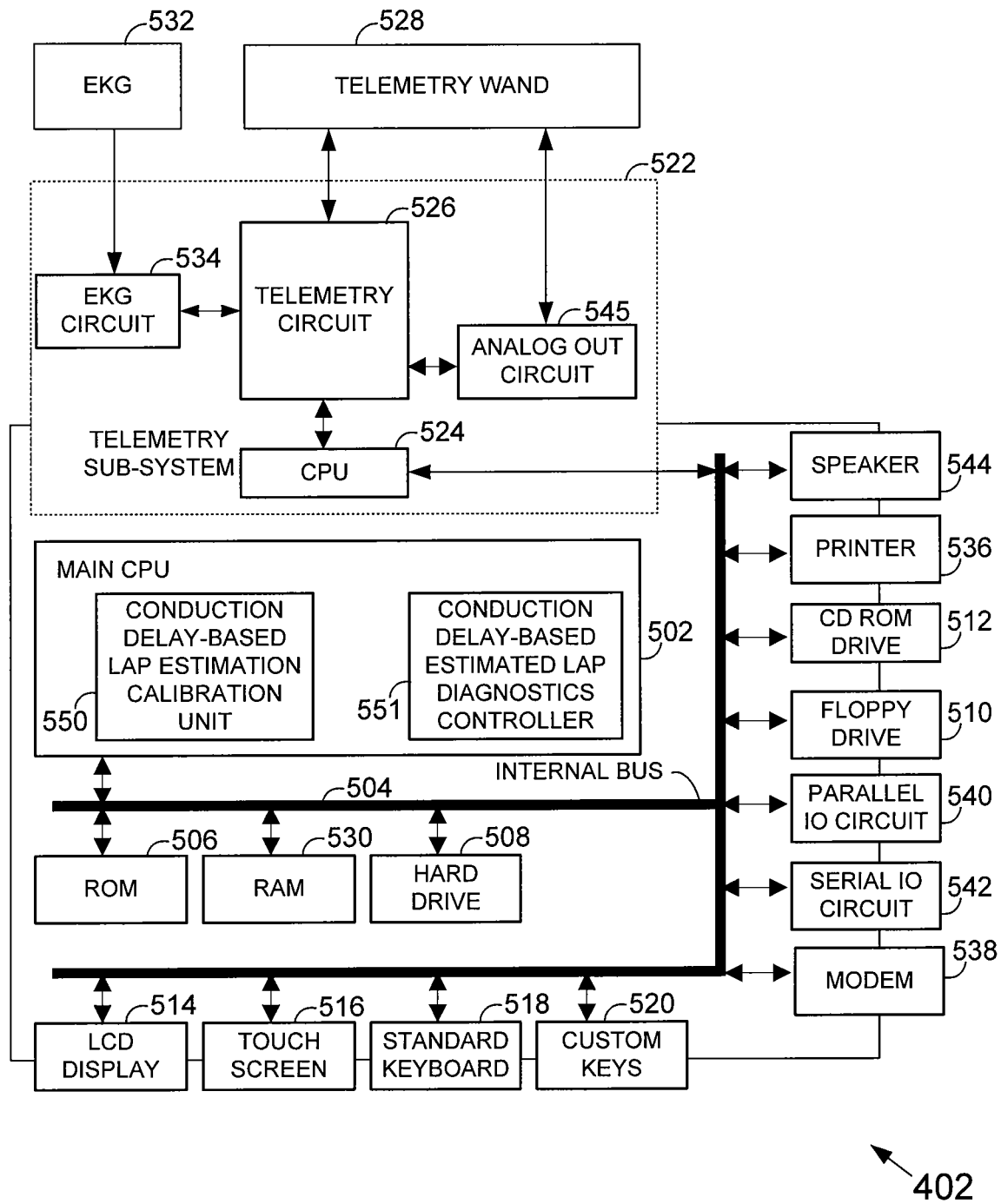
FIG. 16 is a functional block diagram illustrating components of a device programmer of FIG. 15, and in particular illustrating a programmer-based LAP estimation calibration system.

With reference to FIGS. 14 and 15, a description of an exemplary pacer/ICD will now be provided. FIG. 14 provides a simplified block diagram of the pacer/ICD, which is a dual-chamber stimulation device capable of treating both fast and slow arrhythmias with stimulation therapy, including cardioversion, defibrillation, and pacing stimulation, and also capable of estimating LAP or other forms of cardiac pressure using impedance signals. To provide other chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 324 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 324 is designed to receive atrial and ventricular cardiac signals and to deliver left ventricular pacing therapy using at least a left ventricular tip electrode 326 and a LV ring electrode 325, left atrial pacing therapy using at least a left atrial ring electrode 327, and shocking therapy using at least a left atrial coil electrode 328. With this configuration, biventricular pacing can be performed. Although only three leads are shown in FIG. 14, it should also be understood that additional leads (with one or more pacing, sensing and/or shocking electrodes) might be used and/or additional electrodes might be provided on the leads already shown. An interventricular conduction delay 101, already discussed, is also shown in FIG. 14.

A simplified block diagram of internal components of pacer/ICD 10 is shown in FIG. 15. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 340 for pacer/ICD 10, shown schematically in FIG. 15, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 345, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left ventricular ring terminal ($V_L$ RING) 345, a left atrial ring terminal ($A_L$ RING) 346, and a left atrial shocking terminal ($A_L$ COIL) 348, which are adapted for connection to the left ventricular ring electrode 326, the left atrial ring electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($V_R$ COIL) 356, and an SVC shocking terminal (SVC COIL) 358, which are adapted for connection to the right ventricular tip electrode 332, right ventricular ring electrode 334, the $V_R$ coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 15, an atrial pulse generator 370 and a ventricular pulse generator 372 generate pacing stimulation pulses for delivery by the right atrial lead 320, the right ventricular lead 330, and/or the CS lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, CS lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the CS lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV delay, V-V delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 15. The battery 410 may vary depending on the capabilities of pacer/ICD 10. If the system only provides low voltage therapy, a lithium iodine or lithium copper fluoride cell typically may be utilized. For pacer/ICD 10, which employs shocking therapy, the battery 410 should be capable of operating at low current drains for long periods, and then be capable of providing high-current pulses (for capacitor charging) when the patient requires a shock pulse. The battery 410 should also have a predictable discharge characteristic so that elective replacement time can be detected. Accordingly, appropriate batteries are employed.

As further shown in FIG. 15, pacer/ICD 10 is shown as having an impedance measuring circuit 412, which is enabled by the microcontroller 360 via a control signal 414. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 412 is advantageously coupled to the switch 474 so that any desired electrode may be used. The impedance measuring circuit 412 also detects the impedance signals discussed above if ZLAP is to be estimated, in addition to qLAP. That is, impedance measuring circuit 412 is an electrical impedance (Z) detector operative to detect an electrical impedance (Z) signal within the patient along at least one sensing vector wherein impedance is affected by cardiac pressure.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 4-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Insofar as LAP estimation is concerned, the microcontroller includes a conduction delay-based LAP estimation system 401 operative to estimate LAP or other forms of cardiac pressure based on parameters derived from conduction delays using the techniques described above. That is, the estimation system is operative to: measure an electrical conduction delay in the heart of the patient and estimate cardiac pressure within the patient from the electrical conduction delay. In this example, estimation system 401 includes: an LV-RV delay measurement system 403 operative to measure interventricular conduction delays within the patient and an LV-RV-based LAP estimation system 405 operative to estimated LAP from the measured interventricular delays. The estimation system also includes, in this example, an LV-RV-based LV EDV estimation system 407 operative to estimate LV EDV from the measured interventricular delays and an LV-RV-based LV EDP estimation system 409 operative to estimate LV EDP from the measured interventricular delays. Estimation system 401 also includes a re-calibration unit or system 411 operative to re-calibrate the conversion factors discussed above. An LAP-based CHF detection system 415 is provide to detect and track CHF based on LAP. Warning and/or notification signals are generated, when appropriate, by a therapy/warning controller 417 then relayed to the bedside monitor 18 via telemetry system 400 or to external programmer 402 (or other external calibration system.) Controller 417 can also controller an implantable drug pump, if one is provided, to deliver appropriate medications. Controller 417 also controls the adaptive adjustment of CRT parameters and other pacing parameters, as discussed above. Terminals for connecting the implanted warning device and the implanted drug pump to the pacer/ICD are not separately shown. Diagnostic data pertaining to LAP, CHF, therapy adjustments, etc., is stored in memory 394.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

Exemplary External Programmer

FIG. 16 illustrates pertinent components of an external programmer 402 for use in programming the pacer/ICD of FIG. 15 and for performing the above-described calibration techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 402 may also be capable of processing and analyzing data received from the implanted device and from the EKG leads to, for example, render preliminary diagnosis as to medical conditions of the patient or to the operations of the implanted device.

Now, considering the components of programmer 402, operations of the programmer are controlled by a CPU 502, which may be a generally programmable microprocessor or microcontroller or may be a dedicated processing device such as an application specific integrated circuit (ASIC) or the like. Software instructions to be performed by the CPU are accessed via an internal bus 504 from a read only memory (ROM) 506 and random access memory 530. Additional software may be accessed from a hard drive 508, floppy drive 510, and CD ROM drive 512, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 514 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 516 overlaid on the LCD display or through a standard keyboard 518 supplemented by additional custom keys 520, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 402 to retrieve data stored within any implanted devices and to also retrieve EKG data from EKG leads, if any, coupled to the patient. To this end, CPU 502 transmits appropriate signals to a telemetry subsystem 522, which provides components for directly interfacing with the implanted devices, and the EKG leads. Telemetry subsystem 522 includes its own separate CPU 524 for coordinating the operations of the telemetry subsystem. Main CPU 502 of programmer communicates with telemetry subsystem CPU 524 via internal bus 504. Telemetry subsystem additionally includes a telemetry circuit 526 connected to telemetry wand 528, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 534 for receiving surface EKG signals from a surface EKG system 532. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 402 either within a random access memory (RAM) 530, hard drive 508 or within a floppy diskette placed within floppy drive 510. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 402, the implanted devices may be further controlled to transmit additional data in real time as it is detected by the implanted devices, such as additional IEGM data, lead impedance data, and the like. Additionally, or in the alternative, telemetry subsystem 522 receives EKG signals from EKG leads 532 via an EKG processing circuit 534. As with data retrieved from the implanted device itself, signals received from the EKG leads are stored within one or more of the storage devices of the external programmer. Typically, EKG leads output analog electrical signals representative of the EKG. Accordingly, EKG circuit 534 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 502, the programming commands are converted to specific programmable parameters for transmission to the implanted devices via telemetry wand 528 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 536.

Additionally, CPU 502 also preferably includes a conduction delay-based LAP estimation calibration unit 550 operative to perform the calibration procedures described above. CPU 502 also preferably includes a conduction delay-based estimated LAP diagnostics controller 551 operative to control the display of estimated LAP values and related diagnostics. As already noted, physicians are often more familiar with LAP values than conduction delay values and hence benefit from LAP-based diagnostics displays that graphically illustrates changes in LAP within the patient, such as changes brought on by heart failure.

Programmer/monitor 402 also includes a modem 538 to permit direct transmission of data to other programmers via the public switched telephone network (PSTN) or other interconnection line, such as a TI line or fiber optic cable. Depending upon the implementation, the modem may be connected directly to internal bus 504 may be connected to the internal bus via either a parallel port 540 or a serial port 542. Other peripheral devices may be connected to the external programmer via parallel port 540 or a serial port 542 as well. Although one of each is shown, a plurality of input output (IO) ports might be provided. A speaker 544 is included for providing audible tones to the user, such as a warning beep in the event improper input is provided by the physician. Telemetry subsystem 522 additionally includes an analog output circuit 545 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted devices and to reprogram the implanted device if needed. The descriptions provided herein with respect to FIG. 16 are intended merely to provide an overview of the operation of programmer and are not intended to describe in detail every feature of the hardware and software of the programmer and is not intended to provide an exhaustive list of the functions performed by the programmer.

In the foregoing descriptions, LAP or other cardiac pressure values are estimated from conduction delay values. A variety of techniques were set forth for determining or measuring the delay values. In the following section, techniques are set forth for estimating delay values from admittance or impedance measurements. Note, though, that the estimated delay values are not necessarily used to then estimate LAP. Rather, the estimated delay values may be used for any suitable purpose. In particular, heart failure may be tracked based on the estimated delay values. That is, whereas the foregoing set forth techniques inter alia for tracking heart failure based on LAP values estimated from measured conduction delays, the following section sets forth techniques for tracking heart failure based on conduction delays estimated from measured impedance or admittance values. The two general techniques may be used in conjunction, where appropriate.

Admittance/Impedance-Based Delay Estimation Techniques

Turning now to FIGS. 17-20, system and methods for estimating conduction delays from admittance or impedance values and for tracking heart failure based on the estimated conduction delays will be briefly summarized. The examples described here principally exploit measured impedance values. However, as impedance in the reciprocal of admittance, measured admittance values can alternatively be exploited. Briefly, with reference to FIG. 17, impedance values are measured at block 600 from which conduction delay values are estimated at block 602. The delay values are used to detect heart failure events, at block 604, or to perform heat failure trending. A calibration block is also provided for calibrating the impedance to delay estimation procedure. That is, when the delays are estimated via block 602, supervising personnel can verify the estimations are correct by comparing the estimated delays to QuickOpt-based delays obtained in the physician's office. Any difference therebetween can then be used to adjust or calibrated the impedance to delay estimation procedure. Once properly calibrated, impedance measurements (block 608) may be used by the pacer/ICD to estimate conduction delays (block 610), from which heat failure events (or heart failure trends) 612 are detected.

Figure 18:
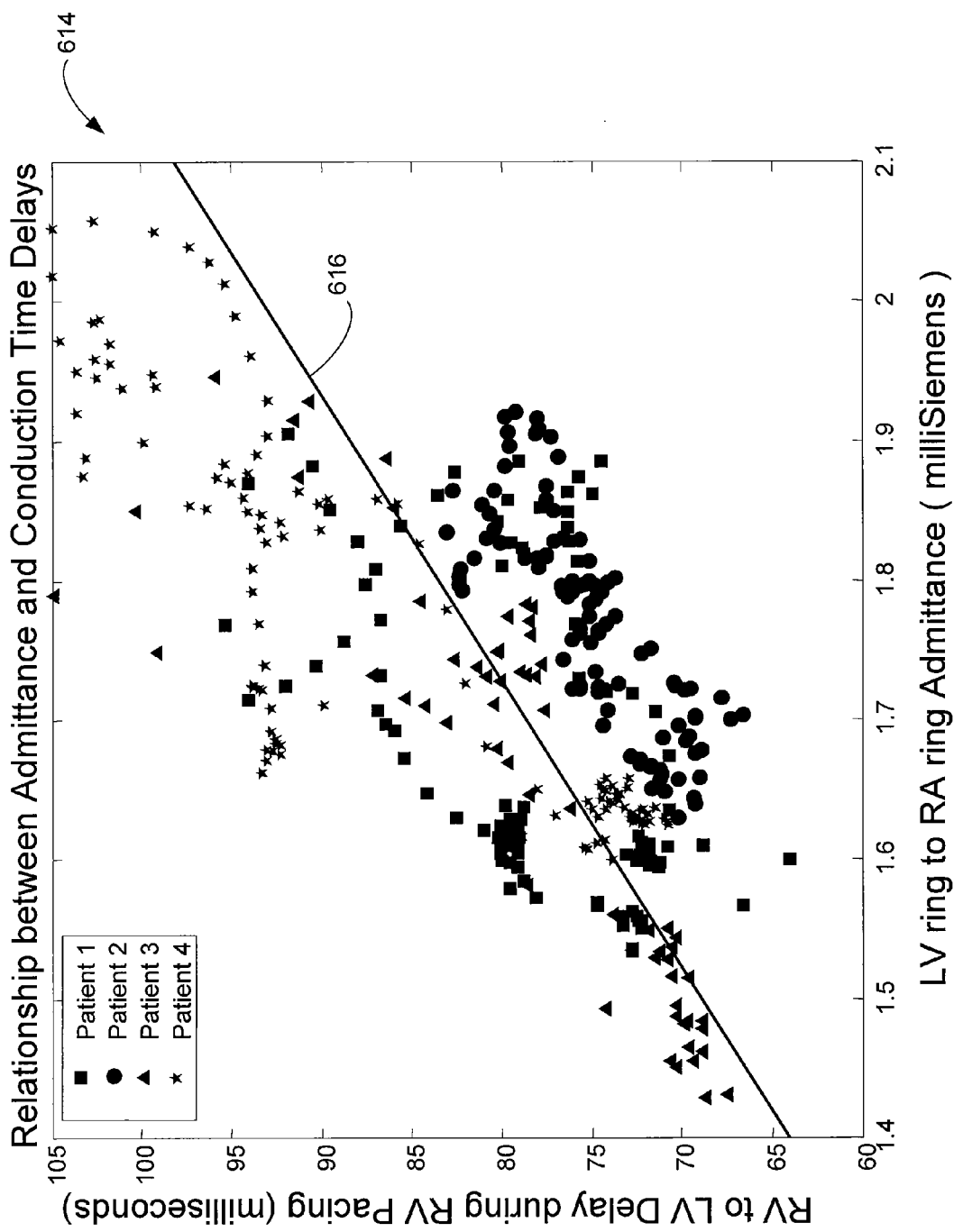
FIG. 18 illustrates a relationship between admittance (i.e. the reciprocal of impedance) and conduction time delays, which is exploited by the technique of FIG. 17.

The estimation of conduction delays based on impedance exploits a generally linear correlation between admittance and conduction time delays, which is illustrated in FIG. 18 by way of graph 614. In particular, the graph shows the relationship between admittance (1/impedance) and VV delay. This example used the impedance vector from the LV ring to the RA ring. The delay was the between the RV and LV while the RV was being paced. The relationship in this example shows a strong linear relationship between the VV delay and LVring-RAring admittance in five patients. Line 616 represents the best-fit line between W delay and admittance given by: VVdelay [ms]=48.712*Admittance [mS]−4.12.

Figure 19:
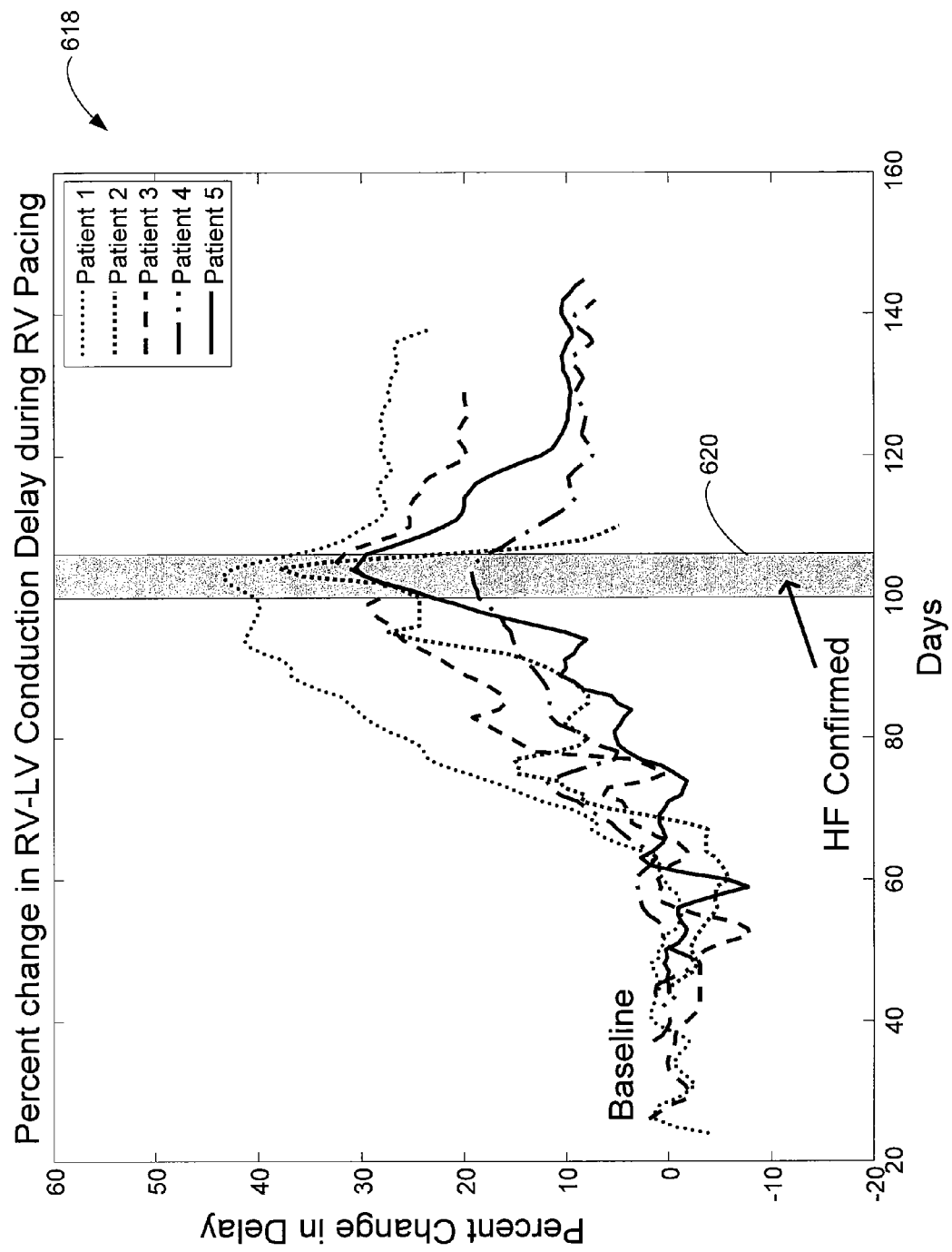
FIG. 19 illustrates changes on conduction time delays that are indicative of heart failure, which may also be exploited by the technique of FIG. 17.

As explained, heart failure can be detected and tracked based on conduction delays. This is illustrated in FIG. 19 by way of graph 618. In this example, developing heart failure caused an increase in the delay between the RV and the LV measured when the RV is paced. Day 100 represents the normalized time when the five patients experienced a HF exacerbation. HF was resolved at day 104 and then patients recovered. The gray shaded area 620 of the graph highlights the time period when heart failure was occurring. Hence, FIG. 19 shows that the delay increased during HF and decreased during recovery. The percent change is referenced to baseline (i.e. zero percent is no HF). The pacer/ICD can be programmed to set a threshold (for instance 20%) to detect HF events. If the percent change in the delays increase above 20%, an alarm can be used to trigger the patient to take corrective action.

Figure 17:
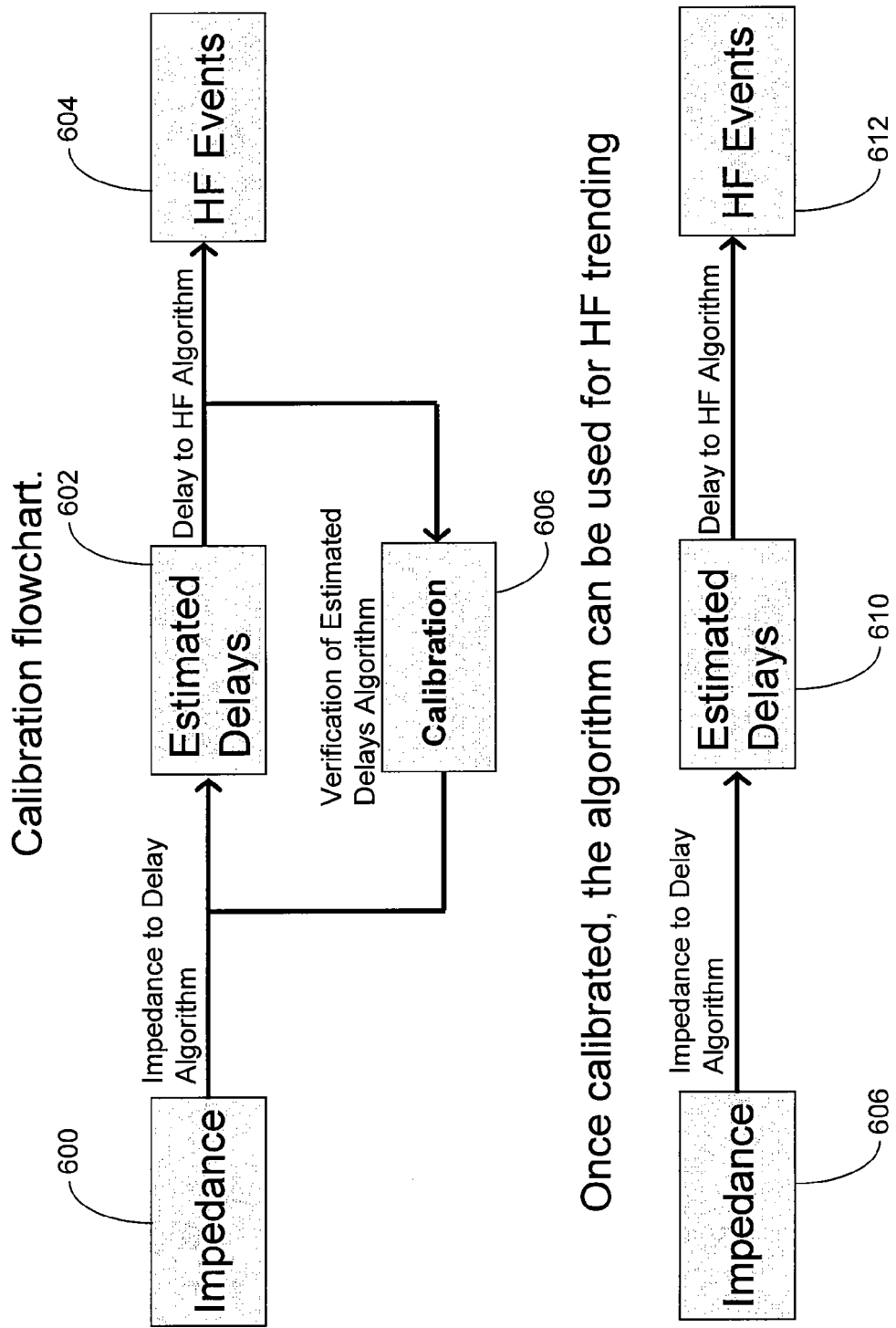
FIG. 17 summarizes a technique for estimating conduction delays based on measured impedance values for use with the system of FIG. 1.
Figure 20:
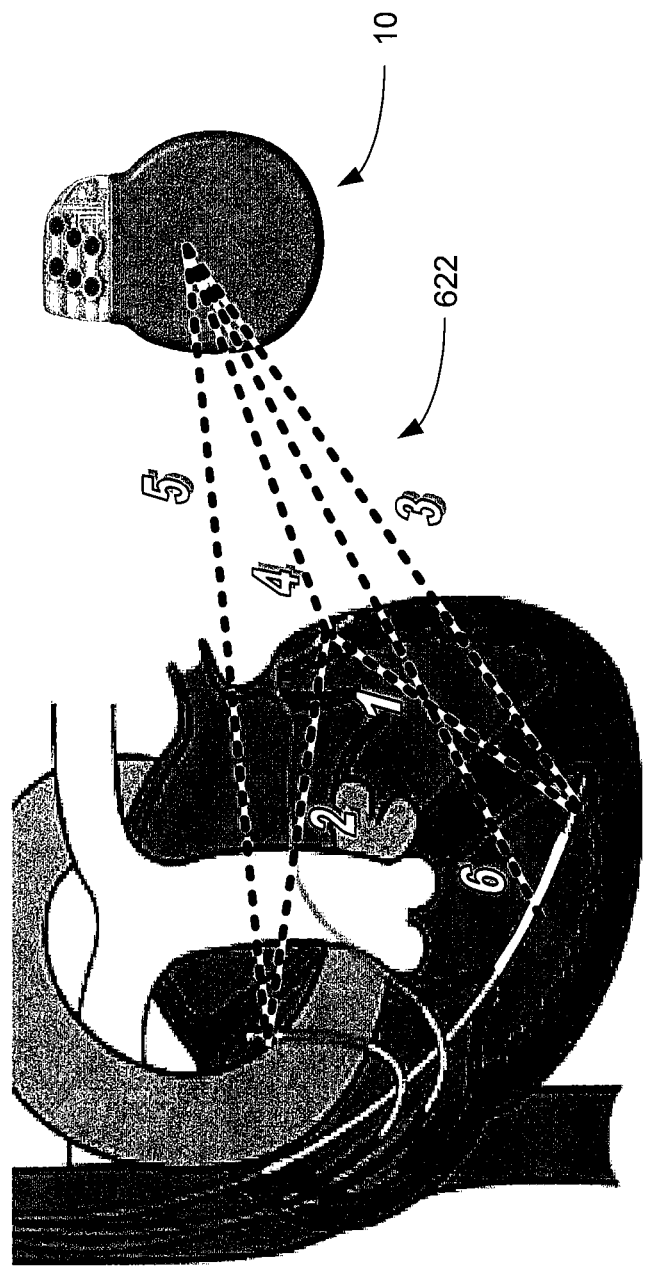
FIG. 20 provides a stylized representation of a heart and particularly illustrates various impedance vectors that may be exploited used to measure impedance for use with the technique of FIG. 17.

As shown in FIG. 20, one or multiple impedance or admittance vectors 622 can be used in either a linear or multi-linear (i.e. quadratic, etc) combination to estimate the conduction delays. The examples of FIG. 20 are as follows: 1: LV ring to RV ring; 2. LV ring to RA ring; 3. RV ring to case; 4. LV ring to case; 5. RA ring to case; and 6. RV coil to case. Multiple different equations can be used to determine the delays. In one example, where admittance values are detected, the relationship between the admittance and delay is quadratic:

$$\text{Delay} = \alpha * adm^2 + \beta * adm + \delta$$

where "adm" refer to admittance and where alpha, beta, and gamma are known constants developed using a training set of data. Multiple admittance values can be used to determine a delay:

$$\text{Delay} = \alpha_1 * adm_1^2 + \beta_1 * adm_1 + \alpha_2 * adm_2^2 + \beta_2 * adm_2 + \delta$$

where admittance vectors 1 and 2 with their corresponding parameters were used to determine the delay. In another embodiment, the estimated delays can be verified each time the patient goes to the physician's office such as with the use of delay algorithm or with special software such as QuickOpt™. When the device is interrogated with the programmer, the programmer would use the QuickOpt procedure to verify the estimated delays offline (FIG. 17).

In general, while the invention has been described with reference to particular embodiments, modifications can be made thereto without departing from the scope of the invention. Note also that the term "including" as used herein is intended to be inclusive, i.e. "including but not limited to".

APPENDIX A

%Setting threshold for find RV
max_rv=max(rv);
mn_rv=mean(rv);
thshld_rv=0.55*(max_rv−mn_rv)+mn_rv; %threshold
I find where the RV crosses the threshold
%Finding when RV crosses threshold
ndx=find(rv>thshld_rv);
dndx=diff([0; ndx]);
sndx=find(dndx>10);
strt_ndx=ndx(sndx);
dndx=diff([ndx; length(rv)]);
endx=find(dndx>10);
end_ndx=ndx(endx);
I find the maximum signal when the V channel crosses the threshold, and call that my ndx
%Finding maximum for index of RV
ndx_rv=zeros(length(strt_ndx),1);
for i=1:length(strt_ndx)
   [jnk,mx_ndx]=max(rv(strt_ndx(i):end_ndx(i)));
   ndx_rv(i)=strt_ndx(i)+mx_ndx−1;
end
Make sure that each V event captures based on size of signal
%Making sure caption occurred
bad_ndx=[ ];
if ndx_lv(end)+25>length(lv)
   ndx_lv(end)=[ ];
end
for i=1:length(ndx_lv)
   mx_lv=max(lv(ndx_lv(i):ndx_lv(i)+12));
   if mx_lv<69
      bad_ndx=[bad_ndx i];
   end
end
ndx_lv(bad_ndx)=[ ];
This next section aligns the LV with the RV to match sure they are

APPENDIX A-continued

```
matched with eachother
%Making sure LV and RV are same length
if ~isempty(ndx_lv) && ~isempty(ndx_rv)
    if length(ndx_rv)~=length(ndx_lv)
        while ndx_rv(1)<ndx_lv(1)
            ndx_rv(1)=[ ];
        end
        while ndx_lv(end)>ndx_rv(end)
            ndx_lv(end)=[ ];
        end
    end
end
if length(ndx_rv)~=length(ndx_lv)
    %disp('error: RV ~= LV: LV')
    %Removing T waves from RV ndx
    diff_rv=diff(ndx_rv);
    diff_ndx=find(diff_rv<100);
    ddndx=diff([0;diff_ndx]);
    diff_ndx=diff_ndx(ddndx~=1);
    ndx_rv(diff_ndx+1)=[ ];
    %Aligning RV with LV indices
    if length(ndx_rv)<length(ndx_lv)
        tmp_ndx=zeros(length(ndx_rv),1);
        bad_ndx=[ ];
        for i=1:length(ndx_rv)
            tmp=find(ndx_lv>ndx_rv(i)-56 & ndx_lv<ndx_rv(i)+90);
            if ~isempty(tmp)
                if length(tmp)>1
                    tmp2=ndx_lv(tmp)-ndx_rv(i);
                    [jnk,tmp3]=min(abs(tmp2));
                    tmp=tmp(tmp3);
                end
                tmp_ndx(i)=ndx_lv(tmp);
            else
                bad_ndx=[bad_ndx i];
            end
        end
        ndx_rv(bad_ndx)=[ ];
        ndx_lv=tmp_ndx;
        ndx_lv(ndx_lv==0)=[ ];
    elseif length(ndx_rv)>length(ndx_lv)
        tmp_ndx=zeros(length(ndx_lv),1);
        bad_ndx=[ ];
        for i=1:length(ndx_lv)
            tmp=find(ndx_rv>ndx_lv(i)-80 & ndx_rv<ndx_lv(i)+80);
            if ~isempty(tmp)
                if length(tmp)>1
                    tmp2=ndx_rv(tmp)-ndx_lv(i);
                    [jnk,tmp3]=min(abs(tmp2));
                    tmp=tmp(tmp3);
                end
                tmp_ndx(i)=ndx_rv(tmp);
            else
                bad_ndx=[bad_ndx i];
            end
        end
        ndx_lv(bad_ndx)=[ ];
        ndx_rv=tmp_ndx;
        ndx_rv(ndx_rv==0)=[ ];
    end
end
```

What is claimed is:

1. A method for controlling a therapy delivered to a patient using an implantable medical device, the method comprising:

measuring an electrical conduction delay in the heart of the patient that is affected by cardiac pressure;

estimating cardiac pressure within the patient from the electrical conduction delay; and controlling a therapy for the patient based on estimated cardiac pressure.

2. The method of claim 1 wherein the implantable device is equipped with an implantable drug pump and wherein drug therapy is controlled based on estimated cardiac pressure.

3. The method of claim 1 wherein therapy is controlled in an effort to maintain the estimated cardiac pressure within a predetermined range representative of healthy pressure values.

4. The method of claim 3 wherein, so long as the estimated cardiac pressure is within the predetermined range representative of healthy pressure values, no therapy adjustments are performed.

5. The method of claim 3 wherein, if the estimated cardiac pressure is within a first predetermined range above healthy pressure values, cardiac pacing parameters are adjusted in an effort to lower the cardiac pressure.

6. The method of claim 5 wherein, if the estimated cardiac pressure is within a second predetermined range above the first range, one or more of the following actions are performed: warning signals are generated indicative of high pressure values; appropriate medications are directly delivered to the patient; instruction signals are generated to instruct the patient to take appropriate medications; instruction signals are generated to instruct the patient to visit a physician.

7. The method of claim 1 wherein the step of adjusting a therapy includes adjusting one or more pacing timing parameters of the implantable medical device to reduce cardiac pressure.

8. The method of claim 7 wherein therapy is adjusted by adjusting an atrioventricular (AV) timing parameter.

9. The method of claim 7 wherein therapy is adjusted by adjusting an interventricular (LV-RV) timing parameter.

10. The method of claim 7 wherein therapy is adjusted by adjusting an intraventricular ($LV_1$-$LV_2$, $RV_1$-$RV_2$) timing parameter.

11. The method of claim 7 wherein therapy is adjusted based on pressure values estimated only during particular patient activity levels as determined in conjunction with an activity sensor.

12. The method of claim 7 wherein therapy is adjusted based on pressure values estimated only while the patient is in a particular posture as determined in conjunction with a position sensor.

13. The method of claim 7 wherein therapy is adjusted based on pressure values estimated only while the patient has a particular blood oxygen saturation level as determined in conjunction with a blood oxygen saturation sensor.

14. The method of claim 7 wherein therapy is adjusted on a beat-by-beat basis.

15. The method of claim 7 wherein the device is equipped to selectively deliver pacing at any of a plurality of pacing sites and wherein the step of adjusting therapy is performed to select particular pacing sites based on the conduction delays.

16. A system for controlling therapy delivered to a patient using an implantable medical device, the system comprising:

an electrical conduction delay measurement unit operative to measure conduction delays within the heart of the patient that are affected by cardiac pressure;

a cardiac pressure estimation unit operative to estimate cardiac pressure within the patient based on the electrical conduction delay; and a therapy controller operative to control therapy based on estimated cardiac pressure.

17. The system of claim 16 wherein the therapy controller is operative to control therapy in an effort to maintain the estimated cardiac pressure within a predetermined range representative of healthy pressure values.

18. The system of claim 17 wherein, so long as the estimated cardiac pressure is within the predetermined range representative of healthy pressure values, the therapy controller makes no therapy adjustments based on the estimated cardiac pressure.

19. The system of claim 18 wherein, if the estimated cardiac pressure is within a first predetermined range above healthy pressure values, the therapy controller is operative to adjust cardiac pacing parameters in an effort to lower the cardiac pressure.

20. The system of claim 19 wherein, if the estimated cardiac pressure is within a second predetermined range above the first range, the therapy controller is operative to perform one or more of the following actions: generate warning signals indicative of high pressure values; deliver appropriate medications directly to the patient via an implantable drug pump; generate instruction signals for transmitting to an external device for instructing the patient to take appropriate medications; generate instruction signals for transmitting to an external device for instructing the patient to visit a physician.

21. A method for detecting a heart failure condition within a patient using an implantable medical device, the method comprising:
 measuring an electrical conduction delay in the heart of the patient that is affected by cardiac pressure;
 estimating cardiac pressure within the patient from the electrical conduction delay; and
 detecting a heart failure condition based on estimated cardiac pressure.

22. The method of claim 21 wherein the implantable device is equipped with a warning device and wherein a warning is generated upon detection of heart failure.

23. The method of claim 22 wherein the implantable device is equipped to transmit signals to an external display device and wherein the warning is transmitted to the external device.

24. A method for estimating cardiac pressure within a patient using an implantable medical device, the method comprising:
 measuring an electrical conduction delay in the heart of the patient;
 estimating cardiac pressure within the patient from the electrical conduction delay; and
 transmitting estimated cardiac pressure values to an external device.

25. The method of claim 24 wherein the external device is equipped to store estimated cardiac pressure values within a database.

26. The method of claim 24 wherein the implantable device is equipped to receive signals from the external device and wherein adjusted pacing parameters are received from the external device.

27. The method of claim 26 wherein the adjusted pacing parameters include cardiac resynchronization (CRT) parameters.

* * * * *